US012070196B2

(12) United States Patent
Barry et al.

(10) Patent No.: US 12,070,196 B2
(45) Date of Patent: Aug. 27, 2024

(54) ARTHROSCOPIC MEDICAL IMPLEMENTS AND ASSEMBLIES

(71) Applicant: Medos International Sarl, Le Locle (CH)

(72) Inventors: Donald E. Barry, Norwood, MA (US); Andre Francisco Guilherme, Raynham, MA (US); Laurent Blanquart, Westlake Village, CA (US); Mark Shainwald, Raynham, MA (US); Robert Thistle, Bridgewater, MA (US)

(73) Assignee: Medos International Sarl, Le Locle (CH)

( * ) Notice: Subject to any disclaimer, the term of this patent is extended or adjusted under 35 U.S.C. 154(b) by 596 days.

(21) Appl. No.: 17/101,259

(22) Filed: Nov. 23, 2020

(65) Prior Publication Data

US 2022/0160221 A1 May 26, 2022

(51) Int. Cl.
*A61B 1/317* (2006.01)
*A61B 1/00* (2006.01)
*A61B 1/05* (2006.01)

(52) U.S. Cl.
CPC .......... *A61B 1/317* (2013.01); *A61B 1/00114* (2013.01); *A61B 1/00117* (2013.01);
(Continued)

(58) Field of Classification Search
CPC . A61B 1/317; A61B 1/00114; A61B 1/00117; A61B 1/05; A61B 2217/007;
(Continued)

(56) References Cited

U.S. PATENT DOCUMENTS 4,674,500 A 6/1987 Desatnick
5,220,911 A 6/1993 Tamura
(Continued)

FOREIGN PATENT DOCUMENTS

WO WO-2019075208 A1 4/2019

OTHER PUBLICATIONS

U.S. Appl. No. 17/101,244, filed Nov. 23, 2020, Donald Barry et al.
(Continued)

*Primary Examiner* — Anh Tuan T Nguyen
*Assistant Examiner* — Shankar Raj Ghimire
(74) *Attorney, Agent, or Firm* — William C. Geary

(57) ABSTRACT

In general, arthroscopic medical implements and assemblies and methods of operating arthroscopic medical implements and assemblies are provided. Devices, systems, and methods are described herein in connection with accessing a surgical site using an arthroscopic medical implement. In an exemplary implementation, an optical sensor of the arthroscopic medical implement can gather and output image data, and an inertial sensor of the arthroscopic medical implement can gather and output orientation data. The orientation data can be used to modify the gathered optical image to maintain a display of the gathered optical image in a predetermined desired orientation before, during, and after any rotation of the arthroscopic medical implement. The arthroscopic medical implement can also include at least one sensor configured to gather and output pressure and/or temperature.

20 Claims, 20 Drawing Sheets

(52) U.S. Cl.
CPC .......... *A61B 1/05* (2013.01); *A61B 2217/005* (2013.01); *A61B 2217/007* (2013.01); *A61B 2562/0247* (2013.01); *A61B 2562/0271* (2013.01)

(58) Field of Classification Search
CPC .... A61B 2562/0247; A61B 2562/0271; A61B 1/015; A61B 1/00066; A61B 1/00119; F04B 43/1253; F04B 43/12
See application file for complete search history.

(56) References Cited

U.S. PATENT DOCUMENTS

| | | | |
|---|---|---|---|
| 5,460,490 A * | 10/1995 | Carr | A61M 1/7415 417/474 |
| 5,554,111 A * | 9/1996 | Morrey | A61M 1/85 604/35 |
| 5,630,799 A * | 5/1997 | Beiser | A61M 3/022 604/67 |
| 5,830,180 A * | 11/1998 | Chandler | A61M 3/022 604/35 |
| 5,881,321 A | 3/1999 | Kivolowitz | |
| 6,097,423 A | 8/2000 | Mattsson-Boze et al. | |
| 6,106,494 A * | 8/2000 | Saravia | A61M 3/0258 604/35 |
| 6,187,026 B1 | 2/2001 | Devlin et al. | |
| 6,471,637 B1 | 10/2002 | Green et al. | |
| 6,832,985 B2 | 12/2004 | Irion et al. | |
| 6,916,286 B2 | 7/2005 | Kazakevich | |
| 7,037,258 B2 | 5/2006 | Chatenever et al. | |
| 7,050,657 B2 | 5/2006 | Yushiya et al. | |
| 7,052,455 B2 | 5/2006 | Hale et al. | |
| 7,134,992 B2 | 11/2006 | Schara et al. | |
| 7,211,042 B2 | 5/2007 | Chatenever et al. | |
| 7,344,494 B2 | 3/2008 | Hoeg et al. | |
| 7,517,314 B2 | 4/2009 | Hoeg et al. | |
| 7,585,273 B2 | 9/2009 | Adler et al. | |
| 7,783,133 B2 | 8/2010 | Dunki-Jacobs et al. | |
| 7,833,152 B2 | 11/2010 | Chatenever et al. | |
| 7,857,792 B2 | 12/2010 | Tachoire et al. | |
| 7,931,588 B2 | 4/2011 | Sarvazyan et al. | |
| 7,956,887 B2 | 6/2011 | Hoeg et al. | |
| 8,033,991 B2 | 10/2011 | Sarvazyan et al. | |
| 8,211,008 B2 | 7/2012 | Henzler | |
| 8,366,607 B2 | 2/2013 | Sullivan et al. | |
| 8,553,975 B2 | 10/2013 | He et al. | |
| 8,817,086 B2 | 8/2014 | Hoeg et al. | |
| 8,834,358 B2 | 9/2014 | Mckinley et al. | |
| 8,928,746 B1 | 1/2015 | Stevrin et al. | |
| 9,033,871 B2 | 5/2015 | Schara et al. | |
| 9,146,576 B2 | 9/2015 | Schmieding et al. | |
| 9,198,643 B2 * | 12/2015 | Bookbinder | A61B 17/00 |
| 9,319,601 B2 | 4/2016 | He et al. | |
| 9,610,007 B2 | 4/2017 | Kienzle et al. | |
| 2002/0049367 A1 | 4/2002 | Irion et al. | |
| 2006/0069311 A1 | 3/2006 | Sullivan et al. | |
| 2006/0073048 A1 * | 4/2006 | Malackowski | A61M 3/0208 417/474 |
| 2007/0055103 A1 | 3/2007 | Hoefig et al. | |
| 2007/0078370 A1 * | 4/2007 | Shener | A61M 3/0258 604/8 |
| 2007/0238931 A1 | 10/2007 | Hanke | |
| 2008/0081079 A1 * | 4/2008 | Cha | A61M 11/02 128/200.23 |
| 2008/0108870 A1 | 5/2008 | Wiita et al. | |
| 2008/0132763 A1 * | 6/2008 | Isaacson | A61B 1/313 600/158 |
| 2008/0146941 A1 | 6/2008 | Dala-Krishna | |
| 2008/0154182 A1 * | 6/2008 | Martin | A61M 1/82 604/27 |
| 2008/0154185 A1 * | 6/2008 | Blight | A61M 3/0216 604/35 |
| 2008/0287738 A1 * | 11/2008 | Adachi | A61B 1/0016 600/118 |
| 2009/0187072 A1 | 7/2009 | Manohara et al. | |
| 2010/0049119 A1 * | 2/2010 | Norman | A61M 3/022 604/31 |
| 2010/0160736 A1 | 6/2010 | Padget et al. | |
| 2012/0033062 A1 | 2/2012 | Bayer | |
| 2012/0101494 A1 * | 4/2012 | Cadouri | A61B 18/148 606/41 |
| 2013/0131585 A1 * | 5/2013 | Eubanks | A61M 25/0021 604/533 |
| 2013/0267892 A1 * | 10/2013 | Woolford | A61B 17/1659 604/319 |
| 2013/0310640 A1 | 11/2013 | Hashiba et al. | |
| 2013/0329006 A1 | 12/2013 | Boles et al. | |
| 2014/0012078 A1 | 1/2014 | Coussa | |
| 2014/0066928 A1 * | 3/2014 | Bennett | H01M 50/262 361/679.01 |
| 2014/0285644 A1 | 9/2014 | Richardson et al. | |
| 2014/0375784 A1 * | 12/2014 | Massetti | A61B 1/05 348/222.1 |
| 2016/0058614 A1 * | 3/2016 | Ross | A61F 9/007 606/107 |
| 2016/0066770 A1 | 3/2016 | Barbato et al. | |
| 2016/0166134 A1 | 6/2016 | Sonnenschein et al. | |
| 2016/0198132 A1 | 7/2016 | He et al. | |
| 2016/0287779 A1 * | 10/2016 | Orczy-Timko | A61M 3/0202 |
| 2016/0330355 A1 | 11/2016 | Tchouprakov et al. | |
| 2016/0367119 A1 | 12/2016 | Ouyang et al. | |
| 2017/0000959 A1 * | 1/2017 | Mantell | A61M 13/006 |
| 2017/0078583 A1 | 3/2017 | Haggerty et al. | |
| 2017/0136209 A1 * | 5/2017 | Burnett | A61M 1/60 |
| 2017/0252099 A1 * | 9/2017 | Orczy-Timko | A61B 17/32002 |
| 2017/0280969 A1 | 10/2017 | Levy et al. | |
| 2017/0290598 A1 * | 10/2017 | Culbert | A61M 25/003 |
| 2017/0311974 A1 * | 11/2017 | Friedrichs | A61B 17/320092 |
| 2018/0160893 A1 | 6/2018 | Truckai et al. | |
| 2019/0134279 A1 * | 5/2019 | Benamou | A61B 90/03 |
| 2019/0328217 A1 | 10/2019 | Moreau et al. | |
| 2019/0374285 A1 | 12/2019 | Hancock et al. | |
| 2020/0000326 A1 * | 1/2020 | Truckai | A61B 1/00094 |
| 2020/0014853 A1 | 1/2020 | Blanquart | |
| 2020/0014855 A1 | 1/2020 | Blanquart | |
| 2020/0100647 A1 | 4/2020 | Craig et al. | |
| 2020/0187768 A1 * | 6/2020 | Shelton | A61B 1/00087 |
| 2020/0196839 A1 | 6/2020 | Pereira et al. | |
| 2020/0375682 A1 | 12/2020 | Kincaid et al. | |
| 2021/0093243 A1 * | 4/2021 | Stanton | A61B 5/024 |
| 2021/0145263 A1 | 5/2021 | Bagley et al. | |
| 2021/0259790 A1 | 8/2021 | Kaiser | |
| 2021/0282628 A1 | 9/2021 | Tortola | |
| 2022/0047292 A1 | 2/2022 | Rousso et al. | |
| 2022/0160220 A1 * | 5/2022 | Barry | A61B 5/067 |
| 2022/0160221 A1 * | 5/2022 | Barry | A61B 1/00117 |
| 2022/0287725 A1 * | 9/2022 | Watanabe | A61B 17/1628 |

OTHER PUBLICATIONS

Omnivision, OVM7695 VGA Product Brief, Aug. 2014 (2 pages).
Extended European Search Report for EP App. No. 21209854.5 mailed Apr. 19, 2022 (8 pages).
Extended European Search Report for EP App. No. 21209956.8 mailed Apr. 28, 2022 (8 pages).

* cited by examiner

ARTHROSCOPIC MEDICAL IMPLEMENTS AND ASSEMBLIES

FIELD

The present disclosure generally relates to arthroscopic medical implements and assemblies and methods of operating arthroscopic medical implements and assemblies.

BACKGROUND

A variety of disorders and injuries can require arthroscopic procedures to repair any soft tissue damage. These procedures often require multiple arthrosporic devices including a camera, fluid source, fluid drainage, and tissue removal means.

For arthroscopic repair procedures, traditional devices and surgical methods suffer from several drawbacks. For example, current arthroscopic devices combine concentrically arranged tubes in order to provide required sub-devices, such as an optical sensor, a light source, and fluid flow and drainage to the working tip of the arthroscopic device. Due to this concentric tube arrangement, rotating seals are required in order to independently operate each sub-device during rotation of the arthroscopic device during a procedure, such as keeping the optical sensor oriented upright. This can make it difficult for an operator during a procedure since multiple hands are required to handle the traditional arthroscopic device in order operate all of the sub-devices properly.

Accordingly, there remains a need for improved devices and methods for arthroscopic procedures.

SUMMARY

In general, arthroscopic medical implements and assemblies and methods of operating arthroscopic medical implements and assemblies are provided.

In one aspect, an arthroscope is provided that in one embodiment includes a handpiece including a proximal end, a distal end, and a longitudinal axis extending therebetween. The arthroscope also includes a shaft extending distally from the handpiece along the longitudinal axis thereof. The shaft is configured to be advanced arthroscopically into a body of a patient, a plurality of lumens extend through the shaft, at least one of the plurality of lumens is configured to pass fluid therethrough, and at least one of the plurality of lumens is configured to have an electrical wire extending therethrough. The arthroscope also includes an optical sensor at a distal portion of the shaft. The optical sensor is configured to gather image data. The arthroscope also includes an inertial sensor configured to gather orientation data that indicates an orientation of the image data gathered by the optical sensor.

The arthroscope can vary in any number of ways. For example, the arthroscope can also include a plurality of input actuators arranged on an outer surface of the handpiece, each of the input actuators can be configured to be actuated by a user and thereby cause a same function to occur regardless of which one of the input actuators is actuated. In at least some embodiments, the function can include providing an irrigation fluid through the at least one of the plurality of lumens configured to pass fluid therethrough, the function can include providing a negative suction pressure through the at least one of the plurality of lumens configured to pass fluid therethrough, and/or the handpiece can be substantially cylindrical and the input actuators can be arranged circumferentially around an entire circumference of the handpiece.

For another example, the orientation data can include both angular orientation information and axis orientation information.

For yet another example, the arthroscope can also include a first electrical wire extending through one of the plurality of lumens, the first electrical wire can be configured to operably couple the optical sensor and a control unit, and the gathered image data can be configured to be transmitted to the control unit using the first electrical wire. In at least some embodiments, the arthroscope can also include a temperature sensor at the distal portion of the shaft that is configured to gather temperature data, the arthroscope can also include a second electrical wire extending through a second one the plurality of lumens, the temperature sensor can be operably coupled to the control unit via the second electrical wire, and the gathered temperature data can be configured to be transmitted to the control unit using the second electrical wire; and/or the arthroscope can also include a pressure sensor at the distal portion of the shaft that is configured to gather pressure data, the arthroscope can also include a second electrical wire extending through a second one the plurality of lumens, the pressure sensor can be operably coupled to the control unit via the second electrical wire, and the gathered pressure data can be configured to be transmitted to the control unit using the second electrical wire.

For still another example, the arthroscope can also include a plurality of fiber optic fibers extending along the shaft and surrounding the optical sensor. In at least some embodiments, the fiber optic fibers can be mounted in a wall of the shaft.

For another example, the arthroscope can also include a lens disposed distal to the optical sensor, and the arthroscope can also include a prism disposed distal to the lens. In at least some embodiments, the prism can be angled in a range of about 30° to about 70°, and, in at least some embodiments, the prism can be mounted on the distal portion of the shaft, the distal portion of the shaft can be configured to pivot relative to a proximal portion of the shaft, and the arthroscope can also include a movement actuator at the handpiece that is configured to be actuated to cause pivoting of the distal portion.

For still another example, the arthroscope can also include an actuation member extending through at least one of the plurality of lumens, the actuation member can be operably coupled to the distal portion of the shaft, the distal portion of the shaft can be configured to pivot relative to a proximal portion of the shaft, and a movement actuator at the handpiece can be configured to be actuated to change a tension of the actuation member and thereby cause pivoting of the distal portion. In at least some embodiments, the movement actuator can include a slider at the handpiece that is configured to be actuated by being slid relative to the handpiece, thereby changing the tension of the actuation member. In at least some embodiments, the movement actuator can include a tensioner at the handpiece that, when actuated, is configured to translate an actuation force along the actuation member to the distal portion. In at least some embodiments, the movement actuator can include a rotatable dial at the handpiece that is configured to be actuated by being rotated relative to the handpiece, thereby changing the tension of the actuation member.

For yet another example, the proximal end of the handpiece can include a connector mateable with a cable assembly that includes electrical, optical, and fluidic conduits each configured to be in communication with one of the plurality of lumens. In at least some embodiments, the connector can be a single connector. In at least some embodiments, the connector can include a connector for each of the electrical, optical, and fluidic conduits.

For still another example, the arthroscope can be substantially symmetrical about the longitudinal axis thereof. For yet another example, the inertial sensor can be at the distal portion of the shaft. For another example, the inertial sensor can be at the handpiece.

In another aspect, a surgical system is provided that in one embodiment includes an arthroscope that includes a handpiece, a shaft, an optical sensor, and an inertial sensor. The handpiece includes a proximal end, a distal end, and a longitudinal axis extending therebetween. The shaft extends distally from the handpiece along the longitudinal axis thereof. The shaft is configured to be advanced arthroscopically into a body of a patient, a plurality of lumens extend through the shaft, at least one of the plurality of lumens is configured to pass fluid therethrough, and at least one of the plurality of lumens is configured to have an electrical wire extending therethrough. The optical sensor is at a distal end of the shaft and is configured to gather image data. The inertial sensor is at the handpiece and is configured to gather orientation data that indicates an orientation of the image data gathered by the optical sensor. The surgical system also includes a control unit configured to receive the gathered image data from the optical sensor, to receive the gathered orientation data from the inertial sensor, and to modify the image data using the orientation data.

The surgical system can vary in any number of ways. For example, the orientation data can include both angular orientation information and axis orientation information.

For another example, the modifying can include rotating an image of the image data to a desired orientation based on the orientation data, and the control unit can be configured to cause the rotated image to be output to a display unit. In at least some embodiments, the control unit can be configured to modify the image data using the orientation data in real time with rotation of the handpiece about a longitudinal axis of the handpiece, and the control unit can be configured to cause the rotated image to be output to the display unit in real time with the rotation of the handpiece.

For still another example, the control unit can include a pump, the surgical system can also include a cartridge configured to releasably couple to the control unit, and the cartridge can include tubing configured to, with the cartridge operably coupled to the control unit, be operably coupled to the pump such that the pump is configured to pump fluid through the cartridge. In at least some embodiments, the tubing can be configured to operably couple to a fluid source containing an irrigation liquid therein, and, with the cartridge operably coupled to the control unit, the pump can be configured to pump the irrigation liquid into the at least one of the plurality of lumens configured to pass fluid therethrough. In at least some embodiments, with the cartridge operably coupled to the control unit, the pump can be configured to cause a suction force to be provided in the at least one of the plurality of lumens configured to pass fluid therethrough.

For yet another example, the surgical system can also include an insertion tool including an obturator and a guide member, the guide member can include a channel in an outer surface thereof configured to releasably seat the obturator therein, the obturator, seated in the channel, can be configured to be advanced through a skin incision, and the shaft of the arthroscope can be configured to be releasably seated in the channel with the guide member positioned in the incision and after the obturator has been advanced through the skin incision and released from the channel.

For still another example, the arthroscope can also include a plurality of input actuators arranged on an outer surface of the handpiece, each of the input actuators can be configured to be actuated by a user and thereby cause a same function to occur regardless of which one of the input actuators is actuated. In at least some embodiments, the function can include providing an irrigation fluid through the at least one of the plurality of lumens configured to pass fluid therethrough, the function can include providing a negative suction pressure through the at least one of the plurality of lumens configured to pass fluid therethrough, and/or the handpiece can be substantially cylindrical and the input actuators can be arranged circumferentially around an entire circumference of the handpiece.

For another example, the arthroscope can also include a first electrical wire extending through one of the plurality of lumens, the first electrical wire can be configured to operably couple the optical sensor and the control unit, and the gathered image data can be configured to be transmitted to the control unit using the first electrical wire. In at least some embodiments, the arthroscope can also include a temperature sensor at the distal end of the shaft that is configured to gather temperature data, the arthroscope can also include a second electrical wire extending through a second one the plurality of lumens, the temperature sensor can be operably coupled to the control unit via the second electrical wire, and the gathered temperature data can be configured to be transmitted to the control unit using the second electrical wire; and/or the arthroscope can also include a pressure sensor at the distal end of the shaft that is configured to gather pressure data, the arthroscope can also include a second electrical wire extending through a second one the plurality of lumens, the pressure sensor can be operably coupled to the control unit via the second electrical wire, and the gathered pressure data can be configured to be transmitted to the control unit using the second electrical wire.

For still another example, the arthroscope can also include a plurality of fiber optics extending along the shaft and surrounding the optical sensor. In at least some embodiments, the fiber optics can be mounted in a wall of the shaft.

For another example, the arthroscope can also include a lens disposed distal to the optical sensor, and the arthroscope can also include a prism disposed distal to the lens. In at least some embodiments, the prism can be angled in a range of about 30° to about 70°, and, in at least some embodiments, the prism can be mounted on a pivotable distal portion of the shaft and the arthroscope can also include a movement actuator at the handpiece that is configured to be actuated to cause pivoting of the pivotable distal portion.

For still another example, the arthroscope can also include a wire extending through at least one of the plurality of lumens, the wire can be operably coupled to a pivotable distal portion of the shaft, and a movement actuator at the handpiece can be configured to be actuated to change a tension of the wire and thereby cause pivoting of the pivotable distal portion. In at least some embodiments, the movement actuator can include a slider at the handpiece that is configured to be actuated by being slid relative to the handpiece, thereby changing the tension of the wire. In at least some embodiments, the movement actuator can include a tensioner at the handpiece that, when actuated, is configured to translate an actuation force along the wire to the pivotable distal portion. In at least some embodiments, the movement actuator can include a rotatable dial at the handpiece that is configured to be actuated by being rotated relative to the handpiece, thereby changing the tension of the wire.

For yet another example, the proximal end of the handpiece can include a connector mateable with a cable assembly that includes electrical, optical, and fluidic conduits each configured to be in communication with one of the plurality of lumens. In at least some embodiments, the connector can be a single connector. In at least some embodiments, the connector can include a connector for each of the electrical, optical, and fluidic conduits.

For still another example, the arthroscope can be substantially symmetrical about the longitudinal axis thereof.

In another embodiment, a surgical system includes an arthroscope, a control unit, and a cartridge. The arthroscope includes a handle, a cable assembly extending proximally from the handle, and an elongate shaft extending distally from the handle. The cable assembly includes a first cable, a second cable, and a cable connector at a proximal end of the cable assembly. A first lumen and a second lumen extend through the shaft. The first lumen is in communication with a first conduit of the first cable, and the second lumen is in communication with a second conduit of the second cable. The control unit is configured to releasably couple to the cable connector. The control unit includes a pump, and, with the control unit releasably coupled to the cable connector, the control unit is configured to provide electrical power to the arthroscope via the first cable and the first conduit. The cartridge is configured to releasably couple to the control unit. The cartridge includes tubing. With the cartridge releasably coupled to the control unit, the pump is configured to cause fluid flow in the tubing, the second conduit, and the second cable.

The surgical system can vary in any number of ways. For example, the tubing can be configured to operably couple to a fluid source containing an irrigation liquid therein, and the fluid flow can include flow of the irrigation liquid. In at least some embodiments, with the cartridge releasably coupled to the control unit and second tubing of the cartridge operably coupled to a surgical tool configured to deliver a suction force to a surgical site, the pump can be configured to cause a suction force to be provided in the second tubing such that the surgical tool delivers the suction force.

For another example, causing the fluid flow can include causing a suction force to be provided in the tubing, the second conduit, and the second cable. In at least some embodiments, the cable assembly can include a third cable, a third lumen can extend through the shaft, the third lumen can be in communication with a third conduit of the third cable, the control unit can include a second pump, the cartridge can include second tubing configured to operably couple to a fluid source containing an irrigation liquid therein, and, with the cartridge releasably coupled to the control unit, the pump can be configured to cause flow of the irrigation liquid in the second tubing, the third conduit, and the third cable.

For yet another example, the arthroscope can include an optical sensor at a distal portion of the shaft, the optical sensor can be configured to gather image data, and the electrical power provided to the arthroscope can be configured to power the optical sensor. In at least some embodiments, the arthroscope can include an inertial sensor configured to gather orientation data that indicates an orientation of the image data gathered by the optical sensor, and the control unit can be configured to receive the gathered image data via a wire extending through the first conduit and the first cable. The inertial sensor can be at the handpiece or at the distal portion of the shaft. In at least some embodiments, the control unit can be configured to modify an image of the received image data using the received orientation data, and can be configured to cause the modified image to be output to a display unit. In at least some embodiments, the modifying can include rotating the image to a predetermined desired orientation based on the orientation data, and/or the control unit can be configured to modify the image using the orientation data in real time with rotation of the handle about a common longitudinal axis of the handle and the shaft and the control unit can be configured to cause the modified image to be output to the display unit in real time with the rotation of the handle.

In another aspect, a surgical method is provided that in one embodiment includes accessing a surgical site with an arthroscope defining a longitudinal axis. A handpiece of the arthroscope includes electrical, optical, and fluidic pathways. The arthroscope is mated with a cable including an electrical conduit in communication with the electrical pathway, an optical conduit in communication with the optical pathway, and a fluidic conduit in communication with the fluidic pathway. The arthroscope includes an optical sensor that is operably coupled to a control unit, and the arthroscope includes an inertial sensor that is operably coupled to the control unit. The surgical method also includes rotating the arthroscope about the longitudinal axis while the control unit causes an optical image of the surgical site to be provided on a display unit based on image data gathered by the optical sensor. The control unit causes an orientation of the optical image to be maintained in a same orientation on the display unit, based on orientation data gathered by the inertial sensor, throughout the rotation of the arthroscope.

The surgical method can have any number of variations. For example, the orientation data can include both angular orientation information and axis orientation information. For another example, the orientation of the optical image can be one of an upright orientation and a sideways orientation. For yet another example, the arthroscope can include a temperature sensor that is operably coupled to the control unit, and, during the rotation of the arthroscope, the control unit can cause temperature information to be provided on the display unit based on temperature data gathered by the temperature sensor. For still another example, the arthroscope can include a pressure sensor that is operably coupled to the control unit, and, during the rotation of the arthroscope, the control unit can cause pressure information to be provided on the display unit based on pressure data gathered by the pressure sensor. For yet another example, the arthroscope can be substantially symmetrical about the longitudinal axis thereof. For another example, the handpiece can be substantially cylindrical.

In another embodiment, a surgical method includes gathering an image of a surgical site using an optical sensor of an arthroscope, gathering an orientation of the arthroscope using an inertial sensor of the arthroscope, and determining if the gathered orientation of the arthroscope matches a predetermined desired orientation. The surgical method also includes, if the gathered orientation does match the predetermined desired orientation, causing the image to be shown on a display unit. The surgical method also includes, if the gathered orientation does not match the predetermined desired orientation, modifying the image based on the gathered orientation and causing the modified image to be shown on a display unit.

The surgical method can vary in any number of ways. For example, the gathering of the image can include gathering a plurality of images during rotation of the arthroscope about a longitudinal axis thereof, the gathering of the orientation can include gathering a plurality of orientations during the rotation of the arthroscope, each of the gathered orientations can correspond to one of the gathered images, and the determining can occur for each of the gathered images with respect to its corresponding gathered orientation. In at least some embodiments, the arthroscope can include a handpiece and a shaft extending distally from the handpiece; during the rotation of the arthroscope, a distal portion of the shaft can be pivoted relative to the longitudinal axis and a proximal portion of the shaft; the longitudinal axis can be defined by the handpiece and the proximal portion of the shaft; and the optical sensor can be located at the distal portion of the shaft. In at least some embodiments, the gathering of the image can include gathering a plurality of additional images, the gathering of the orientation can include gathering a plurality of additional orientations, each of the gathered additional orientations can correspond to one of the gathered additional images, the determining can occur for each of the gathered additional images with respect to its corresponding gathered additional orientation, and the additional images and the additional orientations can be gathered with the distal portion of the shaft not being pivoted relative to the longitudinal axis and the proximal portion of the shaft.

For another example, the surgical method can also include causing, in response to actuation of any one of a plurality of input actuators of the arthroscope that are arranged around a circumference of a handpiece of the arthroscope, at least one of delivering irrigation fluid to the surgical site from a fluid source and through a first inner lumen of the arthroscope, and providing suction at the surgical site through a second inner lumen of the arthroscope. For yet another example, the predetermined desired orientation can be one of an upright orientation and a sideways orientation. For still another example, the surgical method can also include at least one of causing temperature information to be shown on the display unit based on temperature data gathered by a temperature sensor of the arthroscope, and causing pressure information to be shown on the display unit based on pressure data gathered by a pressure sensor of the arthroscope.

In another embodiment, a surgical method includes providing electrical power from a control unit, which is releasably coupled to an arthroscope and is releasably coupled to a cartridge, to provide electrical power to the arthroscope via a first cable. The arthroscope is releasably coupled to the control unit via a cable connector of a cable assembly that also includes the first cable and a second cable, and the cartridge is releasably seated in a cartridge holder of the control unit. The surgical method also includes causing, using a pump of the control unit, fluid flow in tubing of the cartridge and thereby cause fluid flow in the second cable.

The surgical method can have any number of variations. For example, the fluid flow can include flow of an irrigation liquid. In at least some embodiments, the surgical method can also include causing, using a second pump of the control unit, a suction force to be provided in second tubing of the cartridge such that a surgical tool operably coupled to the second tubing delivers the suction force to a surgical site.

For another example, causing the fluid flow can include causing a suction force to be provided in the tubing. In at least some embodiments, the surgical method can also include causing, using a second pump of the control unit, flow of an irrigation liquid in second tubing of the cartridge and thereby case flow of the irrigation liquid in a third cable of the cable assembly.

For yet another example, the surgical method can also include gathering image data using an optical sensor at a distal portion of the arthroscope, the control unit can receive the gathered image data via a wire extending through the first cable, the surgical method can also include gathering orientation data using an inertial sensor. In at least some embodiments, the surgical method can also include the control unit modifying, in real time with performance of a surgical procedure, an image of the received image data using the received orientation data, and the surgical method can also include causing, using the control unit, the modified image to be displayed on a display unit in real time with the performance of the surgical procedure. In at least some embodiments, the modifying can include rotating the image to a predetermined desired orientation based on the orientation data, and/or the modifying and the causing of the modified image to be displayed can occur in real time with rotation of a handle of the arthroscope about a common longitudinal axis of the handle and a shaft of the arthroscope that extends distally from the handle.

BRIEF DESCRIPTION OF DRAWINGS

This disclosure will be more fully understood from the following detailed description taken in conjunction with the accompanying drawings, in which.

DETAILED DESCRIPTION

Figure 1:
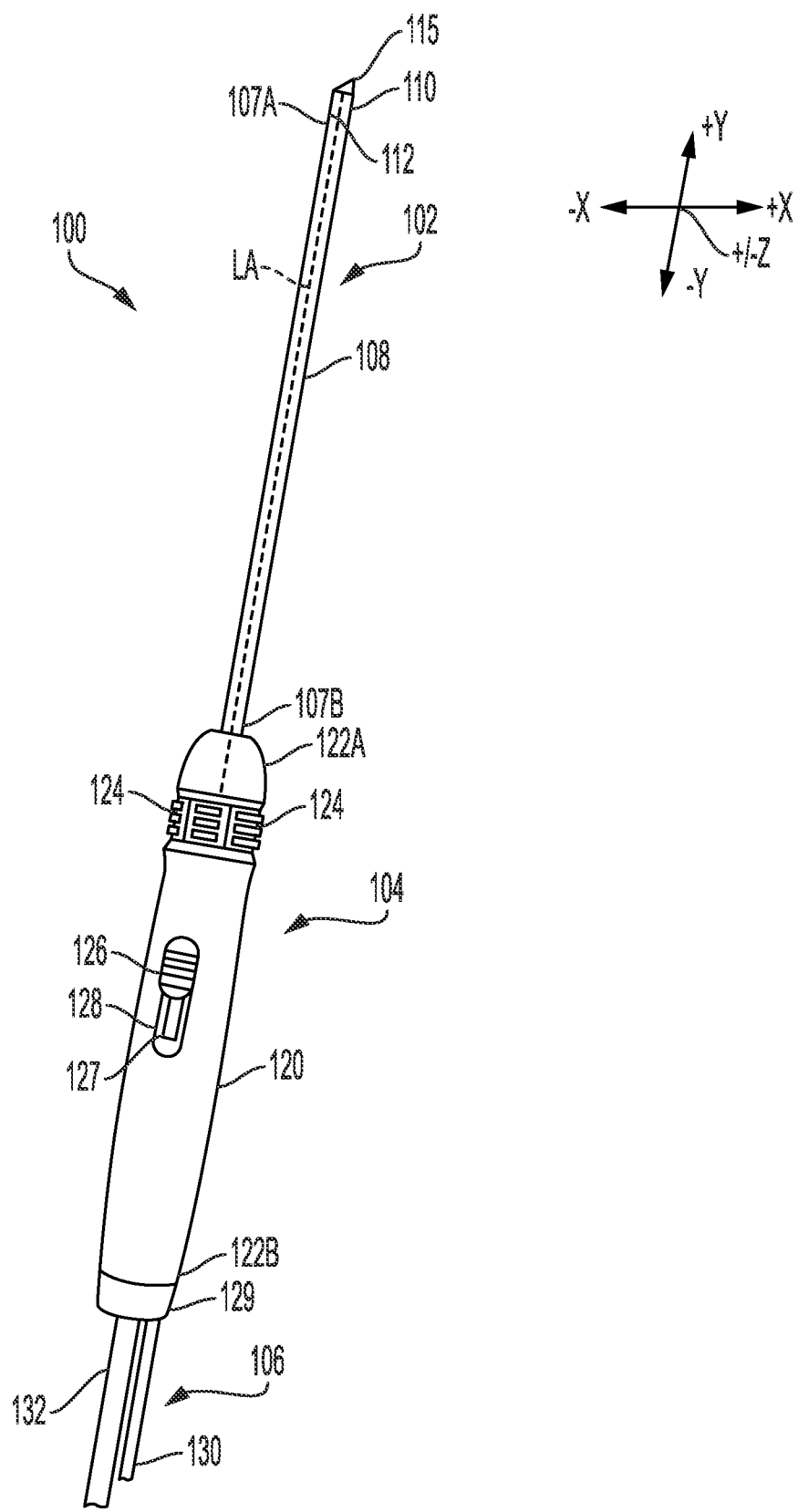
FIG. 1 is a perspective view of one implementation of an arthroscopic medical implement.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, arthroscopic medical implements and assemblies and methods for operating arthroscopic medical implements and assemblies are provided.

The various figures show embodiments of arthroscopic medical implements (also referred to herein as "arthroscopes") and assemblies and methods of the present disclosure. Devices, systems, and methods are described herein in connection with accessing a surgical site using an arthroscopic medical implement. In an exemplary implementation, an optical sensor of the arthroscopic medical implement can gather and output image data, and an inertial sensor of the arthroscopic medical implement can gather and output orientation data. The orientation data can be used to modify the gathered optical image to maintain a display of the gathered optical image in a predetermined desired orientation before, during, and after any rotation of the arthroscopic medical implement. The image data can be image(s) of a surgical site gathered during performance of a surgical procedure such that a surgeon and/or other medical professional may be able to easily interpret conditions at the surgical site by viewing a consistently oriented image regardless of the arthroscopic medical implement's rotational position. The arthroscopic medical implement can also include at least one sensor configured to gather and output pressure and/or temperature. The gathered pressure and/or temperature data can be displayed during performance of a surgical procedure, which may provide useful information to a surgeon and/or other medical professional about a surgical site where the pressure and/or temperature was gathered.

The arthroscopic medical implements disclosed herein may be particularly useful to provide multiple functions to a surgical site while being operated with a single hand of a user. The arthroscopic medical implements can include integrated electrical, optical, and fluidic pathways in a handpiece. Additionally, the arthroscopic medical implement can include an optical sensor, such as at a distal end of a shaft extending from the arthroscopic medical implement's handpiece, that is operably coupled to a control unit. During rotation of the arthroscopic medical implement about a longitudinal axis thereof, an image of the surgical site provided to a display by the optical sensor is maintained in a desired orientation. This modification of the optical image is due to measured orientation data from an inertial sensor of the arthroscopic medical implement, e.g., arranged within the arthroscopic medical implement's handpiece or at the distal end of the arthroscopic medical instrument, configured to determine an orientation of the optical sensor.

Figure 2:
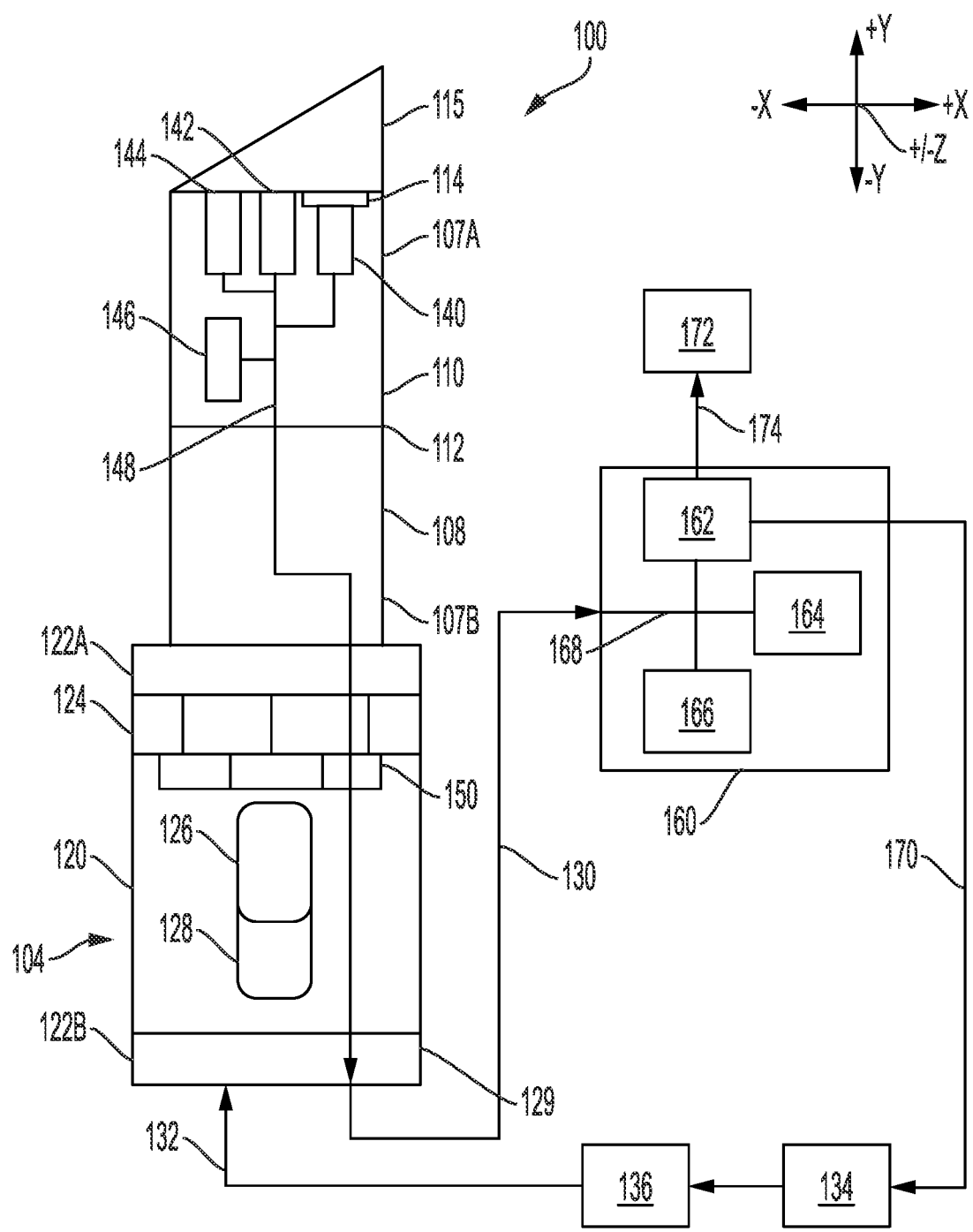
FIG. 2 is a schematic view of the arthroscopic medical implement of FIG. 1.

FIGS. 1 and 2 illustrate one implementation of an arthroscopic medical implement 100. The arthroscopic medical implement 100 is configured to be used in minimally invasive surgical procedures, e.g., arthroscopic procedures for diagnosing and treating joint problems. In one example of using the arthroscope 100, a surgeon inserts a shaft 108 of the arthroscope 100 through a small incision in a patient during a minimally invasive surgical procedure, such as an arthroscopic procedure. An image obtained from within the surgical site using the arthroscope 100 is transmitted to a high-definition video monitor via an optical image sensor of the arthroscope 100, e.g., an optical image sensor arranged on a distal end of the shaft 102. During the procedure, the surgeon holds the arthroscopic medical implement 100 by a handpiece 120 (also referred to herein as a "handle") of the arthroscope 100 to angle the shaft 108 within the surgical site. In an exemplary implementation, the arthroscopic medical implement 100 is used in combination with at least one secondary tool, such as a shaver or other treatment device for tissue or bone. The secondary tool(s) can be inserted into the surgical site through a secondary incision.

In general, the arthroscopic medical implement 100 includes a shaft assembly 102, a handpiece assembly 104, and a cable assembly 106. The shaft assembly 102 includes a shaft 108 extending from a handpiece 120 of the handpiece assembly 104 along a common longitudinal axis LA of the shaft assembly 102 and the handpiece assembly 104. Thus, as shown in FIGS. 1 and 2, the arthroscope 100 has an inline design in which the shaft 108 and the handpiece 120 are axially aligned with one another. The inline design may facilitate easy, predictable user rotation of the arthroscopic medical implement 100 about the longitudinal axis LA. As also shown in FIG. 1, the shaft 108 and the handpiece 120 are substantially symmetrical about the longitudinal axis LA. The longitudinal axis LA is thus a neutral axis. A person skilled in the art will appreciate that a configuration may not be precisely symmetrical but nevertheless be considered substantially symmetrical due to any number of factors, such as manufacturing tolerances and sensitivity of measurement equipment. The shaft 108 and the handpiece 120 being substantially symmetrical may facilitate easy, predictable user rotation of the arthroscopic medical implement 100 about the longitudinal axis LA, may help reduce damage to the patient at a skin incision in which the shaft 108 is positioned because the shaft 108 will predictably rotate about the longitudinal axis LA in the incision, and/or may help reduce damage to tissue and/or other matter inside the patient's body in which the shaft 108 is positioned because the shaft 108 will predictably rotate about the longitudinal axis LA inside the patient's body.

Figure 3A:
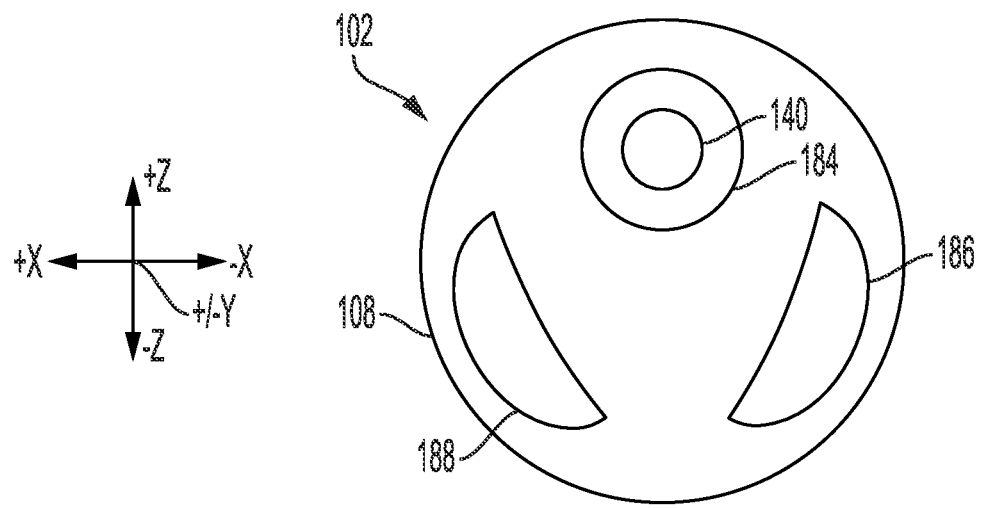
FIG. 3A is a distal end view of one implementation of a tip of the arthroscopic medical implement of FIG. 1.

The shaft 108 includes a distal end 107A and a proximal end 107B. As shown in FIG. 3A, a plurality of lumens 184, 186, 188 extend through the shaft 108. The plurality of lumens 184, 186, 188 are internal to the shaft 108 and can have a variety of configurations in order to provide various functions to and/or from the surgical site. In an exemplary implementation, a first one of the lumens 186 is configured to selectively provide an irrigation fluid therethrough to a surgical site, a second one of the lumens 188 is configured to provide a negative suction pressure therethrough to the surgical site, and a third one of the lumens 184 is used to carry one or more electrical connectors, such as one or more data and power cables, to one or more sensors arranged at the distal end 107A of the shaft 108. For example, in an exemplary implementation, an optical sensor 140 is arranged at the distal end 107A of the shaft 108, such as on a pivotable portion 110 of the shaft 108 and within the third lumen 184, with the one or more electrical connectors being operably coupled to the optical sensor 140. One or more actuation members can also be carried by the third lumen 184 (or in a fourth lumen), as discussed further below.

The locations, sizes, and shapes of the lumens 184, 186, 188 shown in FIG. 3A can be different in other implementations. For example, the fluid lumens 186, 188 in this illustrated implementation each have a half-moon cross-sectional shape but can have other cross-sectional shapes, such as circular, ovular, etc. For another example, the lumens 184, 186, 188 in this illustrated implementation are each radially offset from the longitudinal axis LA, but in other implementations a one of the lumens, e.g., the electrical lumen 184, can be aligned with the longitudinal axis LA while the other two lumens, e.g., the fluid lumens 186, 188, are radially offset from the longitudinal axis LA. For yet another example, while each of the fluid lumens 186, 188 are configured to provide a different fluid function in this implementation with the first lumen 186 providing irrigation and the second lumen 188 providing suction, in other implementations, each of the fluid lumens 186, 188 can be configured to provide suction, each of the fluid lumens 186, 188 can be configured to provide irrigation, or the fluid functions of the lumens 186, 188 can be reversed with the second lumen 188 providing irrigation and the first lumen 186 providing suction.

The shaft 108 being rotatable with the handpiece 120 allows for the plurality of lumens 184, 186, 188 to rotate with the handpiece 120. The fluid lumens 186, 188 may therefore be rotatable without having to pass through any rotatable seals. Rotatable seals are traditionally used in devices providing irrigation and/or suction but are susceptible to fluid leaks during rotation and/or caused by rotation. The arthroscope 100 not including any rotatable seals through which the fluid lumens 186, 188 pass thus eliminates the possibility of leaks at any such rotatable seal. Additionally, seals can be heavy, so the arthroscope 100 not including rotatable seals may therefore make the arthroscope 100 lighter than traditional tools providing irrigation and/or suction, which may make the arthroscope 100 less tiring for a user to handle and/or easier for a user to handle with one hand for rotation, actuation, etc.

Figure 3B:
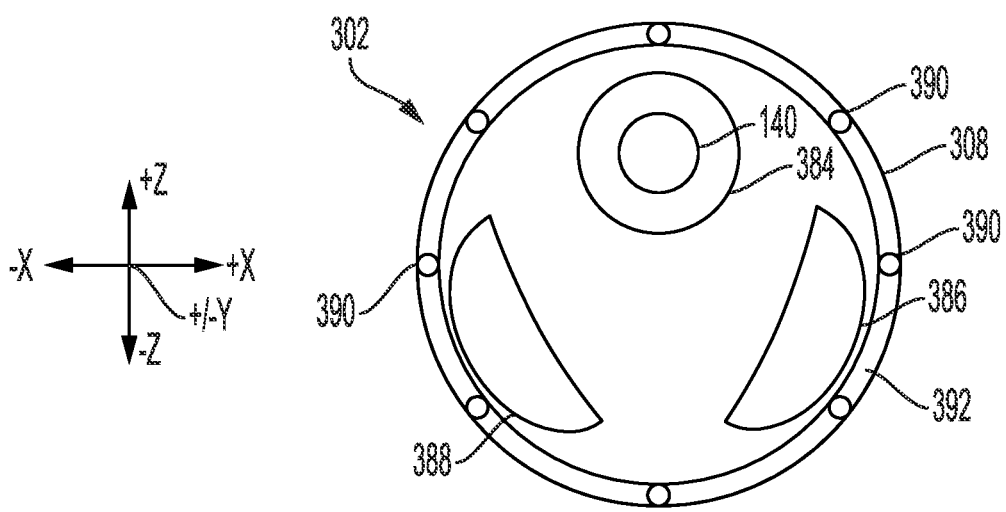
FIG. 3B is a distal end view of another implementation of the tip of the arthroscopic medical implement of FIG. 1.

FIG. 3B illustrates another implementation of the shaft 102 in the form of a shaft 308 of an arthroscope's shaft assembly 302 with a plurality of lumens 384, 386, 388 extending through the shaft 308. The shaft assembly 302 and the shaft 308 are configured and used similar to the shaft assembly 102 and the shaft 108, respectively, of FIGS. 1 and 2. The lumens 384, 386, 388 are configured and used similar to the lumens 184, 186, 188, respectively, of FIG. 3A. In this illustrated implementation, a plurality of lights 390 are arranged within the shaft 308 and extend therethrough. The lights 390 are fiber optic fibers in this illustrated implementation, but other lights such as LEDs, etc. can be used with appropriate electronic lead(s) for the lights arranged within the shaft 308. The lights 390 are arranged around a perimeter of the shaft 308 and are configured to provide light directed distally, which may help illuminate a surgical site and/or reduce shadows and thereby allow the optical sensor 140 to gather clearer, more easily viewable images. The lights 390 are arranged equidistantly and radially around the perimeter of the shaft 308 and thus surround the optical sensor 140. The lights 390 are mounted in a wall 392 of the shaft 308 but can be otherwise assembled in the shaft 308. The lights 390 being mounted in the wall 392 allows the shaft 308 and the lights 390 (at least as fiber optic fibers) be co-extruded. The lights 390 are operably coupled to an external light source and/or a control unit 160, which is shown in FIG. 2 and discussed further below. The control unit 160 is configured to control activation of the lights 390, e.g., to turn illumination on, and deactivation of the lights 390, e.g., to turn illumination off. The illustrated implementation includes eight lights 390, but an arthroscope can include another number of lights 390. Including a plurality of lights 390 instead of only one light may help ensure that the optical sensor's field of view is entirely illuminated regardless of a rotational orientation of the shaft 308 and regardless of whether or not a pivotable portion (if present) of the shaft 308 is pivoted.

Figure 3C:
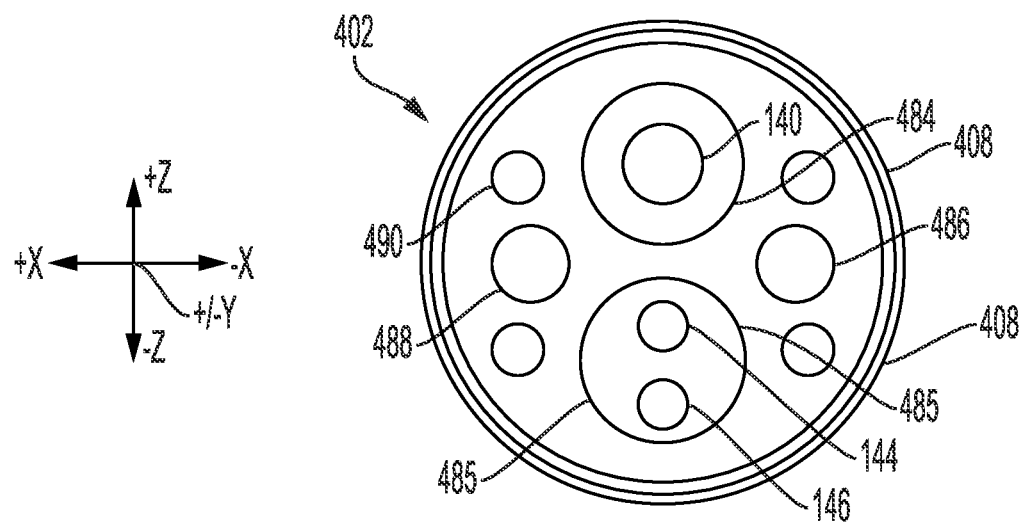
FIG. 3C is a distal end view of yet another implementation of the tip of the arthroscopic medical implement of FIG. 1.

FIG. 3C illustrates another implementation of the shaft 102 in the form of a shaft 408 of an arthroscope's shaft assembly 402 with a plurality of lumens 484, 486, 488 extending through the shaft 408. The shaft assembly 402 and the shaft 408 are configured and used similar to the shaft assembly 102 and the shaft 108, respectively, of FIGS. 1 and 2. The lumens 484, 486, 488 are configured and used similar to the lumens 184, 186, 188, respectively, of FIG. 3A. In this illustrated implementation, the fluid lumens 486, 488 each have a circular cross-sectional shape instead of a half-moon cross-sectional shape. In this illustrated implementation, a fourth lumen 185 extends through the shaft 408. The fourth lumen 485 is an electrical lumen, similar to the third lumen 184, used to carry one or more electrical connectors, such as one or more data and power cables, to one or more sensors arranged at a distal end of the shaft 408. The one or more sensors in this illustrated implementation are the optical sensor 140 and the pressure and temperature sensors 144, 146 discussed above but other sensors can be used. Also in this illustrated implementation, a plurality of lights 490 are arranged within the shaft 408 and extend therethrough. The lights 490 are configured and used similar to the lights 390 of FIG. 3B.

Figure 3D:
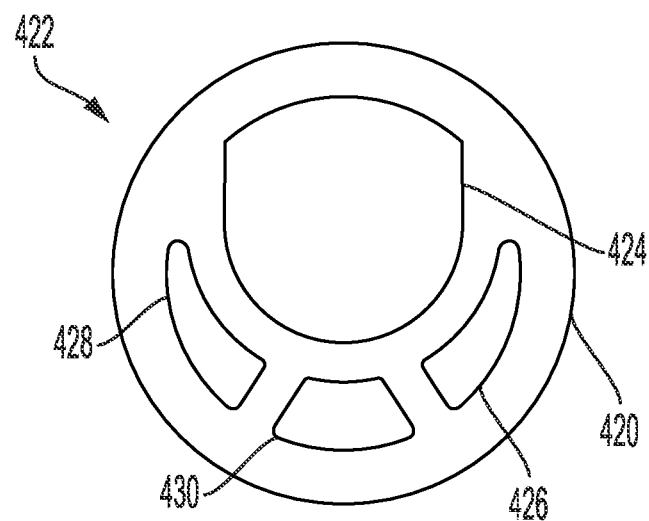
FIG. 3D is a distal end view of still another implementation of the tip of the arthroscopic medical implement of FIG. 1.

FIG. 3D illustrates another implementation of the shaft 102 in the form of a shaft 420 of an arthroscope's shaft assembly 422 with a plurality of lumens 424, 426, 428, 430 extending through the shaft 420. The shaft assembly 422 and the shaft 420 are configured and used similar to the shaft assembly 102 and the shaft 108, respectively, of FIGS. 1 and 2. The lumens 424, 426, 428 are configured and used similar to the lumens 184, 186, 188, respectively, of FIG. 3A. The fourth lumen 430 is configured and used similar to the fourth lumen 485 of FIG. 3C. In this illustrated implementation, the electrical lumen 424 has an irregular cross-sectional shape instead of a circular cross-sectional shape, the fluid lumens 426, 428 each have a tapering arc cross-sectional shape instead of a half-moon cross-sectional shape, and the fourth lumen 430 has an irregular cross-sectional shape instead of a circular cross-sectional shape.

Referring again to FIGS. 1 and 2, the pivotable portion 110 of the shaft 108 is at a distal portion of the shaft 108 and is configured to pivot at a pivot point 112 relative to the handpiece assembly 104 and relative to a proximal portion of the shaft 108 that is proximal to the pivot point 112. The pivoting action of the pivotable portion 110 may allow for a greater field of view at a surgical site with the arthroscopic medical implement 100 inserted within a surgical site. With the pivotable portion 110 pivoted at the pivot point 112 relative to the handpiece 120 and relative to the proximal portion of the shaft 108, the handpiece 120 and the proximal portion of the shaft 108 retain their inline configuration relative to one another. The pivot connection between the pivotable portion 110 and the proximal portion of the shaft 108 can be achieved in any of a variety of ways, such as by using a hinge joint (e.g., a living hinge or other hinge), a pivot pin secured in a pivot hole, etc. In other implementations, the shaft 108 does not include the pivotable portion 110 such that the shaft 108 has a fixed zero-angle along the longitudinal axis LA and such that the arthroscope 100 has a fixed inline design defined by the handpiece 120 and the shaft 108.

As mentioned above, the arthroscope 100 is configured to be used in arthroscopic surgical procedures. The shaft 108 can thus have a size that facilitates its use in an arthroscopic surgical procedure in which a joint is examined and/or operated upon in a minimally invasive manner. For example, an outer diameter of the shaft 108 can be in a range of about 3 mm to about 8 mm. For another example, an outer diameter of the shaft 108 can be in a range of about 5 mm to about 7 mm. For yet another example, the outer diameter of the shaft 108 can be about 6 mm. A person skilled in the art will appreciate that a value may not be at a precise value but nevertheless be considered to be about that value due to any number of factors, such as manufacturing tolerances and sensitivity of measurement equipment.

In an exemplary implementation, the shaft 108 is made from one or more biocompatible materials, and the handpiece 120 is made from one or more biocompatible materials. Examples of biocompatible materials that may be used for the shaft 108 and/or the handpiece 120 include stainless steel, e.g., stainless steel of grade 316 or 304, and thermoplastic, e.g., polycarbonate, acrylonitrile butadiene styrene (ABS), polycarbonate/ABS (PC/ABS) blends, etc. In an exemplary implementation in which the shaft 108 and the handpiece 120 are made from thermoplastic, the shaft 108 and the handpiece 120 can include extruded thermoplastic tubing with conduits for communicating electrical and fluidic circuits. It is practical to co-extrude different materials such as wires and fiber optic cable in order to simplify construction of the arthroscope 100.

The handpiece assembly 104 of the arthroscopic medical implement 100 is configured to be handheld by a user to operate and manipulate the arthroscope 100. In an exemplary implementation, the handpiece assembly 104 includes a substantially cylindrical handpiece 120. A person skilled in the art will appreciate that a shape may not be precisely cylindrical but nevertheless be considered substantially cylindrical due to any number of factors, such as manufacturing tolerances and sensitivity of measurement equipment. The handpiece 120 being substantially cylindrical may facilitate handling of the arthroscope 100 by providing a shape easy for a user to hold securely with one hand. The handpiece 120 can, however, have other shapes, such as bulb or pear-shaped, hourglass-shaped, etc. As mentioned above, in an exemplary implementation, the handpiece 120 is substantially symmetrical about the longitudinal axis LA, which can be achieved by shapes such as cylindrical, bulb or pear-shaped, and hourglass-shaped.

The handpiece 120 includes a distal end 122A and a proximal end 122B, with the longitudinal axis LA extending between the distal and proximal ends 122A, 122B.

The handpiece 120 includes at least one input actuator 124 configured to control a variety of functions of the arthroscopic medical implement 100. As in this illustrated implementation, the handpiece 120 can include a plurality of input actuators 124 arranged on a surface of the handpiece 120 to facilitate user access thereof. The plurality of input actuators 124 are circumferentially arranged on the handpiece 120 such that the input actuators 124 completely surround the handpiece 120. Due to this circumferential arrangement of the input actuators 124, a surgeon or other user of the arthroscope 100 can easily interact with the input actuators 124 independent of a rotational position of the handpiece 120. The input actuators 124 are configured to be actuated to activate a function of the arthroscopic medical implement 100, such as providing an irrigation fluid through one of the lumens of the shaft 108. The input actuators 124 can have a variety of configurations, such as a button configured to be actuated by being pressed by a user (as in this illustrated implementation in which a plurality of buttons are arranged circumferentially around the handpiece 120), a lever or switch configured to be actuated by being moved by a user from a first position to a second position, a dial configured to be rotated by a user from a first position to a second position, a slider configured to be actuated by being slid within a channel from a first position to a second position, etc.

Figure 4A:
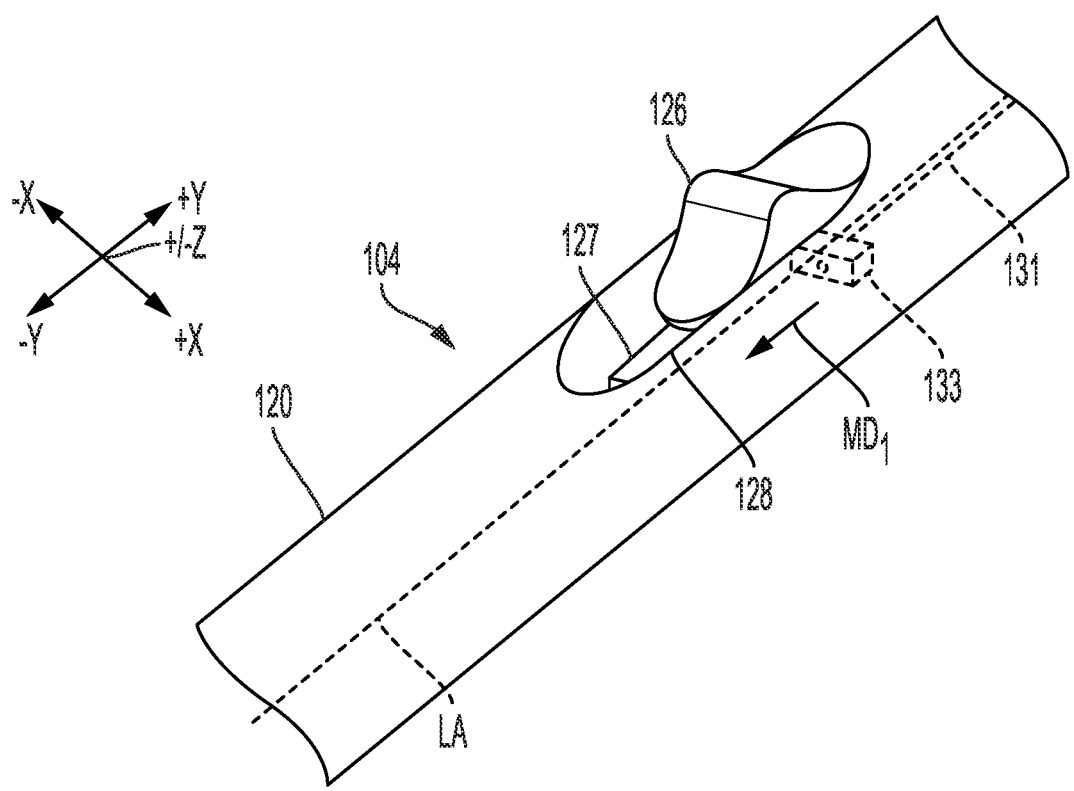
FIG. 4A is a partial perspective view of one implementation of a movement actuator of the arthroscopic medical implement of FIG. 1.
Figure 4B:
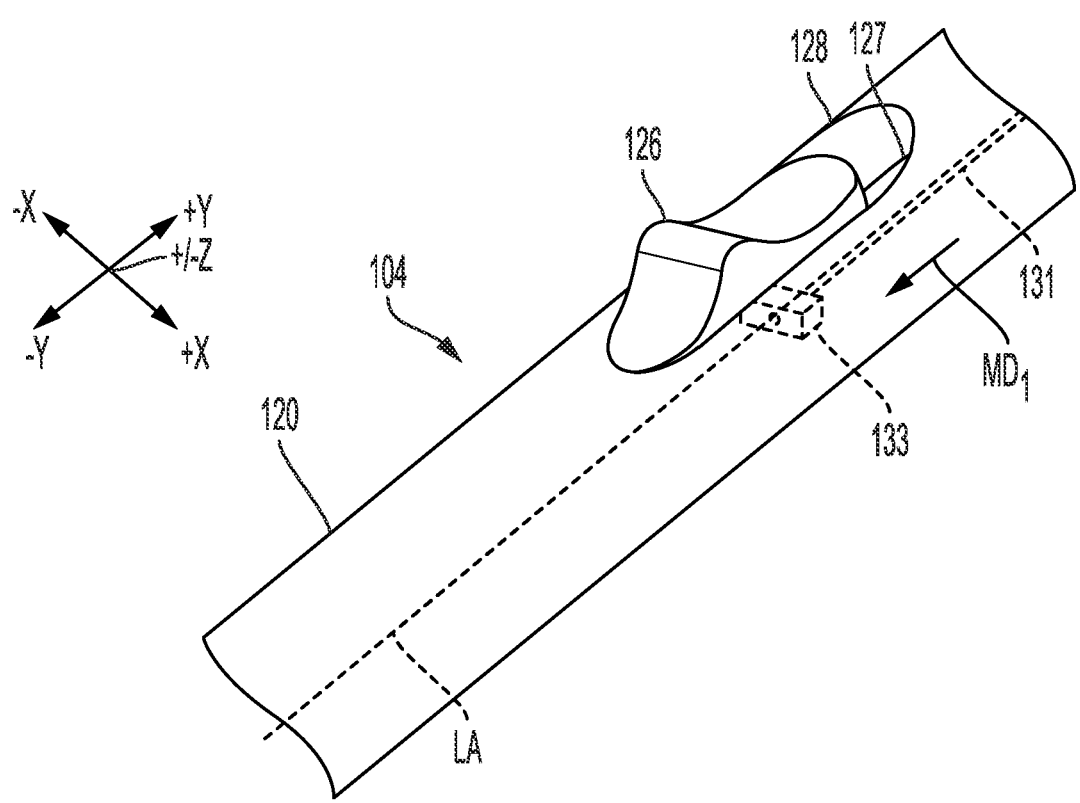
FIG. 4B is a partial perspective view of the movement actuator of FIG. 4A.

The handpiece 120 includes a movement actuator 126 arranged thereon, as also shown in FIGS. 4A and 4B. The movement actuator 126 and the input actuator(s) 124 are arranged on the handpiece 120 to allow a user to operate the input actuators 124 and the movement actuator 126 with a single hand that is holding the handpiece 120 without the user needing a second hand to actuate any of the input actuators 124 or to actuate the movement actuator 126, which may free the user's second hand for other surgical tasks, and without the user having to put down the handpiece 120 and re-grip the handpiece 120 between an actuation of the input actuator 124 and an actuation of the movement actuator 126, which may save time during performance of a surgical procedure and/or more quickly allow for a desired action to occur since the user need not rearrange their grip of the handpiece 120 to cause a desired actuation.

The movement actuator 126 is configured to be actuated to pivot the pivotable portion 110 of the shaft 108. In an exemplary implementation, actuation of the movement actuator 126 translates an actuation force along an actuation member 131, e.g., a wire, a rod, etc., extending through one of the lumens 184, 186, 188 of the shaft 108 to the pivotable portion 110 arranged at the distal end 107A of the shaft 108. The movement actuator 126 can have a variety of configurations. As in this illustrated implementation, the movement actuator 126 can include a slider arranged within a channel 128 on the handpiece 120, with the slider 126 being configured to be actuated by being slid longitudinally within the channel 128. Other examples of the movement actuator 126 includes a button configured to be actuated by being pressed by a user, a lever or switch configured to be actuated by being moved by a user from a first position to a second position, a dial configured to be rotated by a user from a first position to a second position, etc.

The channel 128 includes a gap 127 arranged at a bottom of the channel 128. The gap 127 is configured to allow the movement actuator 126 to be secured to the actuation member 131 via a mount 133. The actuation member 131 is a wire in this illustrated implementation. The wire 131 extends longitudinally along the arthroscope 100 and, more particularly, distally from the handpiece 120 and through the third lumen 184 of the shaft 108 to the pivotable portion 110 of the shaft 108. However, as mentioned above, the actuation member 132 can extend through a fourth lumen of the shaft 108 instead of through the third lumen 184 in which the one or more electrical connectors extend. The actuation member 131 is secured to the pivotable portion 110, e.g., a distal end of the actuation member 131 attached to a proximal end of the pivotable portion 110.

Figure 4C:
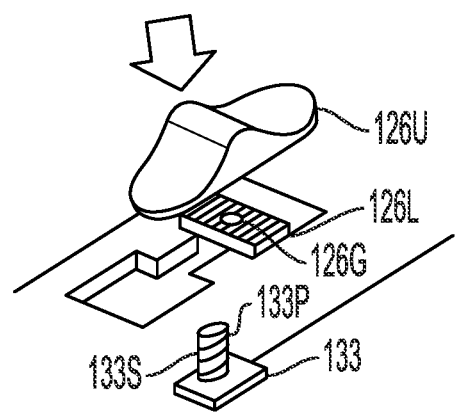
FIG. 4C is a perspective, exploded view of a portion of the arthroscopic medical implement and the movement actuator of FIG. 4A.

FIG. 4C illustrates one implementation of securing the actuation member 131 to the movement actuator 126 using the mount 133. The movement actuator 126 includes an upper portion 126U configured to be handled by a user, and a lower portion 126L with an opening 126G formed therein. The mount 133 includes an upwardly-extending pin 133P configured to extend through the opening 126G and securely seat in an opening (obscured in FIG. 4C) formed in the upper portion 126U, such as by being seated therein via press fit, via corresponding threads on the pin 133P and the upper portion's opening, using adhesive, etc. A spring 133S is coiled around the pin 133P in this illustrated implementation, which may help secure the pin 133P in the upper portion's opening.

FIGS. 1 and 4A illustrate the movement actuator 126 in a first position, which corresponds to the pivotable portion 110 not being pivoted. With the movement actuator 126 in the first position, the wire 131 is in a non-tensioned state. The default state of the wire 131 is in the non-tensioned state, which allows the default state of the movement actuator 126 to be the first position. FIG. 4B illustrates the movement actuator 126 in a second position, which corresponds to the pivotable portion 110 being pivoted. With the movement actuator 126 in the second position, the wire 131 is in a tensioned state. As the movement actuator 126 is actuated to move from the first position to the second position, e.g., as a user moves the slider 126 proximally along the channel 128, the mount 133 operably coupled to the movement actuator 126 also moves proximally. The proximal movement of the movement actuator 126 thus causes tension to be applied to the wire 131 that is also operably coupled to the mount 133. The tension is applied to the wire 131 in a first longitudinal movement direction $MD_1$, which is proximally in this illustrated implementation. The tension causes the pivotable portion 110 to pivot at the pivot point 112 by the wire 131 pulling proximally on the pivotable portion 110. Similarly, as the movement actuator 126 moves from the second position to the first position in a second longitudinal movement direction that is opposite to the first longitudinal movement direction $MD_1$, e.g., distally, the tension on the wire 131 decreases. The decreasing tension causes the pivotable portion 110 to pivot back toward its inline position, which the pivotable portion 110 reaches when the movement actuator 126 reaches its first position.

The default state of the movement actuator 126 allows the movement actuator 126 to be in the first position without a surgeon or other user needing to hold the movement actuator 126 in the first position. The pivotable portion 110 can thus remain in its inline state unless otherwise desired by the surgeon or other user. The movement actuator 126 can be configured to be manually held in any position within the channel 128 up to and including the second position, thereby allowing the pivotable portion 110 to be pivoted at any angle up to its maximum possible angular position relative to the longitudinal axis LA. Alternatively or in addition, the movement actuator 126 can be configured to be locked in position within the channel 128 at one or more preset positions. For example, the arthroscope 100 can include a locking mechanism configured to lock the movement actuator 126 in the second position. The locking mechanism can have any of a variety of configurations. For example, the locking mechanism can include a protrusion formed on one of the shaft 108 and the movement actuator 126 being configured to automatically releasably engage a depression formed in the other of the shaft 108 and the movement actuator 126 and to be automatically disengaged from one another when the movement actuator 126 is moved from the second position. For another example, the locking mechanism can include a clip on one of the shaft 108 and the movement actuator 126 being configured to automatically releasably engage a portion of the other of the shaft 108 and the movement actuator 126 and to be automatically disengage that portion when the movement actuator 126 is moved from the second position. For yet another example, the locking mechanism can include a first magnet on or in the movement actuator 126 and a second magnet on or in the shaft 108 that is configured to magnetically engage the first magnet when in operative distance thereof such that the movement actuator 126 is held in the second position with the first and second magnets magnetically attracted to one another and able to be released by the second position by moving the movement actuator 126 from the second position toward the first position. Regardless of the configuration of the locking mechanism configured to lock the movement actuator 126 in the second position, the movement actuator 126 can be configured to be manually held in any selected position between the first and second positions. Alternatively, the movement actuator 126 can be configured to be locked in one or more additional positions between the first and second positions. For example, the locking mechanism can include a protrusion formed on one of the shaft 108 and the movement actuator 126 being configured to automatically releasably engage each of a plurality of depressions formed in the other of the shaft 108 and the movement actuator 126, with each depression corresponding to a different position at which the movement actuator 126 can be locked. For another example, the locking mechanism can include a depression formed in one of the shaft 108 and the movement actuator 126 being configured to automatically releasably engage each of a plurality of protrusions formed on the other of the shaft 108 and the movement actuator 126, with each protrusion corresponding to a different position at which the movement actuator 126 can be locked. For yet another example, the locking mechanism can include a first magnet on or in the movement actuator 126 and a plurality of additional magnets on or in the shaft 108 that is configured to magnetically engage the first magnet when in operative distance thereof such that the movement actuator 126 is held in position with the first magnet magnetically attracted to one of the plurality of additional magnets.

Figure 5A:
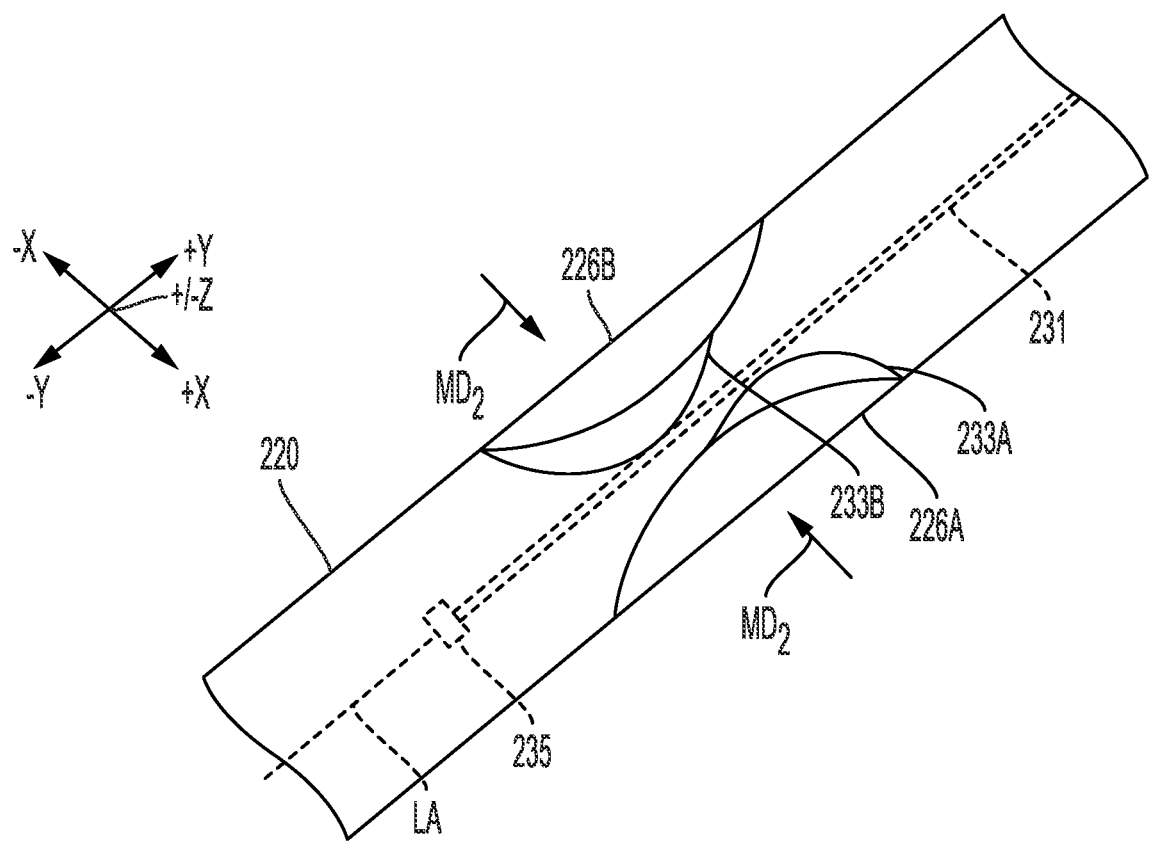
FIG. 5A is a partial perspective view of one implementation of a movement actuator of the arthroscopic medical implement of FIG. 1.
Figure 5B:
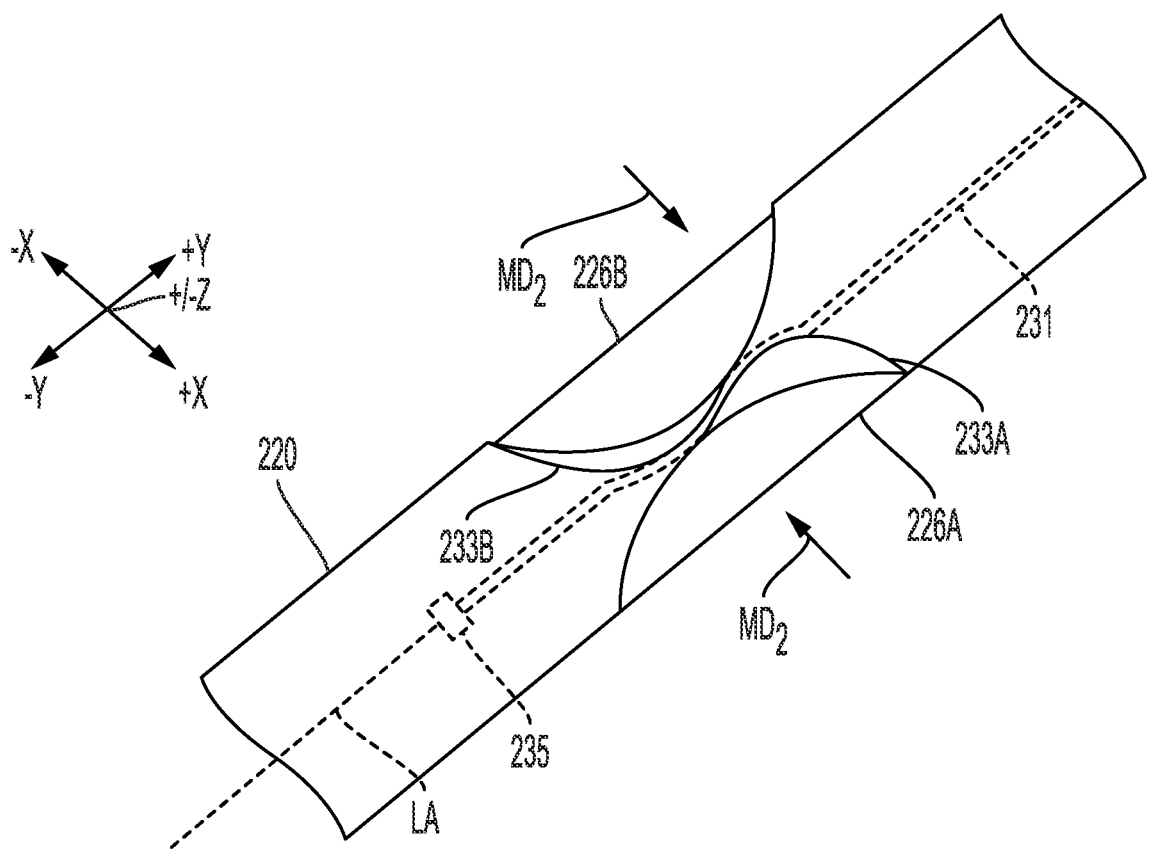
FIG. 5B is a partial perspective view of the movement actuator of FIG. 5A.

As mentioned above, the movement actuator 126 is shown as a slider in FIGS. 1, 4A, and 4B. FIGS. 5A and 5B illustrate another implementation of the movement actuator 126 in the form of a pair of buttons 226A, 226B arranged within a handpiece 220. The handpiece 220 is configured and used similar to the handpiece 120. An actuation member 231, which in this illustrated implementation is a wire configured and used similar to the wire 131, is secured within the handpiece 220 via a mount 235, which is configured and used similar to the mount 133. Each of the buttons 226A, 226B includes a tensioner 233A, 233B. The tensioners 233A, 233B are configured to selectively engage the wire 231 to change tension of the wire 231 and thus cause pivoting of the pivotable portion 110.

FIG. 5A illustrates the movement actuator 226A, 226B in a first position, which corresponds to the pivotable portion 110 not being pivoted. With the movement actuator 226A, 226B in the first position, the wire 231 is in a non-tensioned state. FIG. 5B illustrates the movement actuator 226A, 226B in a second position, which corresponds to the pivotable portion 110 being pivoted. With the movement actuator 226A, 226B in the second position, the wire 231 is in a tensioned state. As the movement actuator 226A, 226B is actuated the movement actuator 226A, 226B moves from the first position to the second position, e.g., as a user squeezes each of the buttons 226A, 226B radially inward in a first movement direction $MD_2$ that is substantially perpendicular to the longitudinal axis LA, tension is applied to the wire 231. More particularly, as the buttons 226A, 226B are squeezed, the tensioners 233A, 233B move into contact with the wire 231 and create a tension in the wire 231 by deforming the wire 231 against curved, convex surfaces of the tensioners 233A, 233B that face radially inward. The deformation of the wire 231 causes the wire 231 to apply a proximal force to the pivotable portion 110, thereby causing the pivotable portion 110 to pivot at the pivot point 112 similar to that discussed above regarding the wire 131. Release of the buttons 226A, 226B causes the tension to be released, thereby allowing the pivotable portion 110 to again pivot at the pivot point 112 and return to its inline position.

A default state of the movement actuator 226A, 226B allows the movement actuator 226A, 226B to be in the first position without a surgeon or other user needing to hold the movement actuator 226A, 226B in the first position. The pivotable portion 110 can thus remain in its inline state unless otherwise desired by the surgeon or other user. The movement actuator 226A, 226B can be biased to the default state with a bias element, such as spring, an elastic band, etc., configured to bias the movement actuator 226A, 226B to the first position. For example, the arthroscope can include a first bias element, which is configured to bias the first button 226A radially outward so the first button 226A is in the first position, and a second bias element, which is configured to bias the second button 226B radially outward so the second button 226B is in the first position.

The movement actuator 226A, 226B can be configured to be manually held in any position up to and including the second position, thereby allowing the pivotable portion 110 to be pivoted at any angle up to its maximum possible angular position relative to the longitudinal axis LA. Alternatively or in addition, the movement actuator 226A, 226B can be configured to be locked in position relative to the handpiece 220 at one or more preset positions. For example, the arthroscope can include a locking mechanism configured to lock the movement actuator 226A, 226B in the second position. The locking mechanism can have any of a variety of configurations, similar to that discussed above with respect to the movement actuator 126. Regardless of the configuration of the locking mechanism configured to lock the movement actuator 226A, 226B in the second position, the movement actuator 226A, 226B can be configured to be manually held in any selected position between the first and second positions. Alternatively, the movement actuator 226A, 226B can be configured to be locked in one or more additional positions between the first and second positions, similar to that discussed above with respect to the movement actuator 126.

Figure 6A:
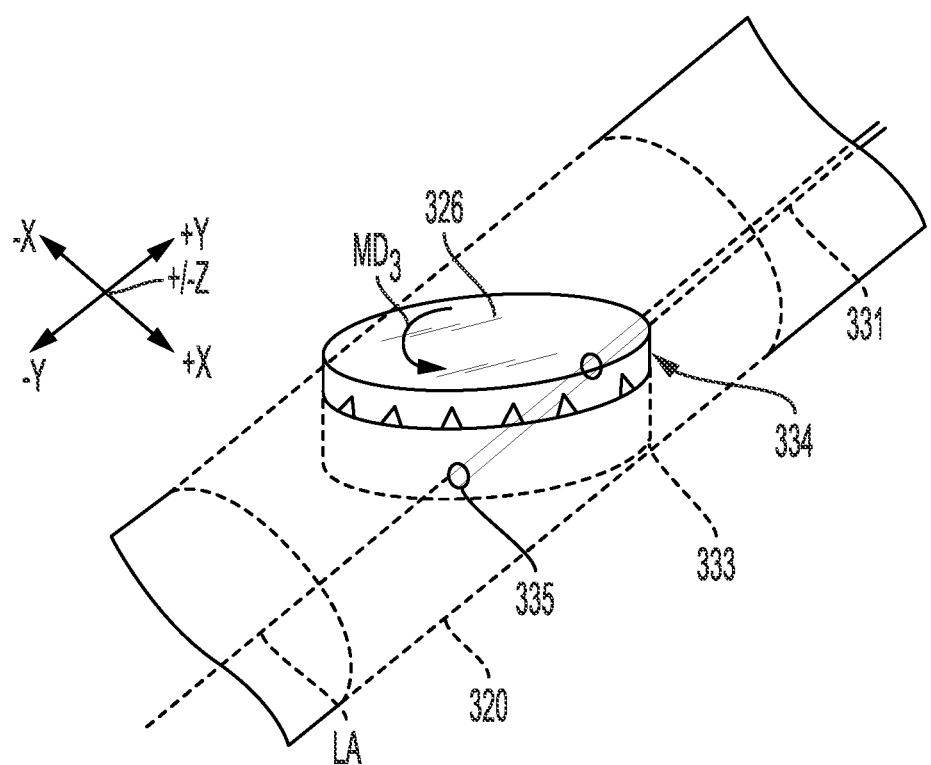
FIG. 6A is a partial perspective view of another implementation of the movement actuator of the arthroscopic medical implement of FIG. 1.
Figure 6B:
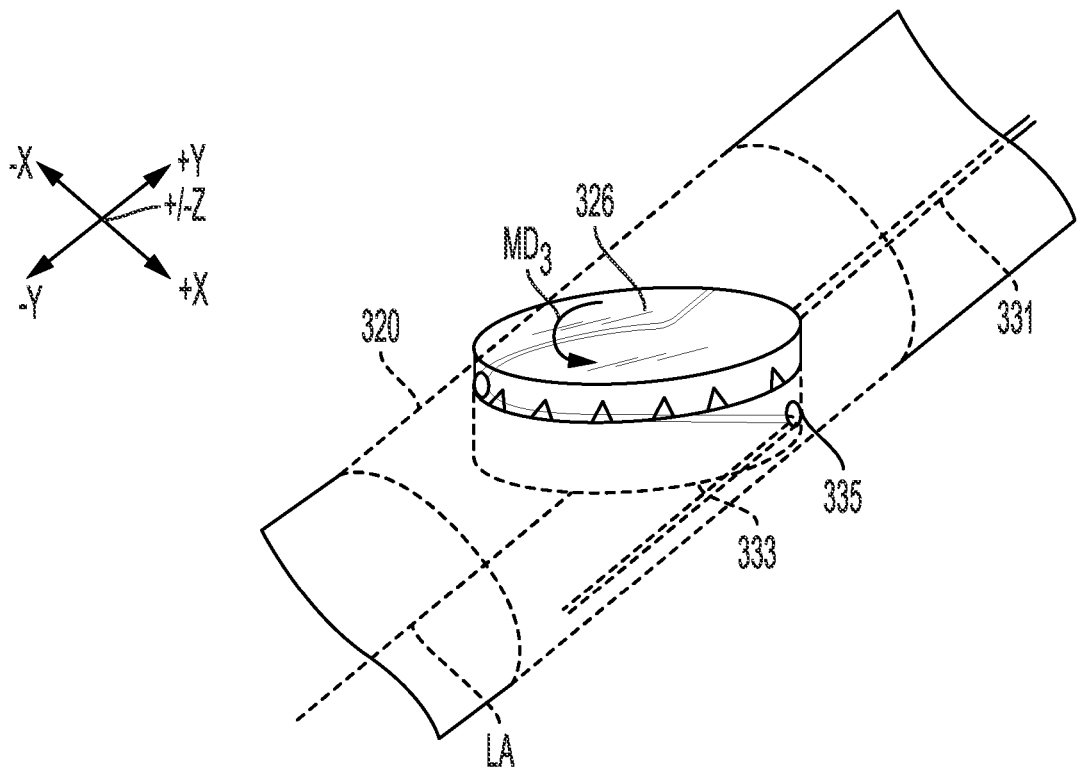
FIG. 6B is a partial perspective view of the movement actuator of FIG. 6A.

FIGS. 6A and 6B illustrate another implementation of the movement actuator 126 as a movement actuator 326 in the form of a rotatable dial arranged within a handpiece 320. The handpiece 320 is configured and used similar to the handpiece 120. The movement actuator 326 is movably seated in an aperture 334 formed in the handpiece 320. An actuation member 331, which in this illustrated implementation is a wire configured and used similar to the wire 131, is secured within the handpiece 320 by being secured to a bottom portion 333 of the rotatable dial 320 that is disposed within the handpiece 320. FIGS. 6A and 6B illustrate the wire 331 secured to a mount 335 in the bottom portion 333, such as by being welded to the mount 335, tied to the mount 335, crimped by the mount 335, etc. The mount 335 can be an interior surface of the bottom portion 333 or can be a separate element secured to the bottom portion 333. The bottom portion 333 includes an opening 336 therein that is located about 180° around the rotatable dial 326 from the mount 335. The wire 331 extends through the opening 336, across the rotatable dial 326 within the bottom portion 333, and is secured to the mount 335. The rotatable dial 326 is configured to be actuated by being rotated, thereby changing the tension on the wire 331 to pivot the pivotable portion 110 at the pivot point 112.

FIG. 6A illustrates the movement actuator 326 in a first position, which corresponds to the pivotable portion 110 not being pivoted. With the movement actuator 326 in the first position, the wire 331 is in a non-tensioned state, which allows the default state of the movement actuator 326 to be the first position. The default state of the wire 331 is in the non-tensioned state, which allows the default state of the movement actuator 326 to be the first position. FIG. 6B illustrates the movement actuator 326 in a second position, which corresponds to the pivotable portion 110 being pivoted. With the movement actuator 326 in the second position, the wire 331 is in a tensioned state. As the movement actuator 326 is actuated the movement actuator 326 moves from the first position to the second position, e.g., as a user rotates the rotatable dial in a first movement direction $MD_3$, tension is applied to the wire 331 as the wire 331 deforms by spooling along an outer surface of the bottom portion 333 of the rotatable dial 326. The tension causes the wire 331 to apply a proximal force to the pivotable portion 110, thereby causing the pivotable portion 110 to pivot at the pivot point 112 similar to that discussed above regarding the wire 131. Release of the rotatable dial 326 causes the tension to be released, thereby allowing the pivotable portion 110 to again pivot at the pivot point 112 and return to its inline position as the rotatable dial 326 rotates in a second movement direction that opposite to the first movement direction $MD_3$. The first movement direction $MD_3$ is counterclockwise and the second movement direction is clockwise in this illustrated implementation, but the first movement direction $MD_3$ can be clockwise and the second movement direction can be counterclockwise.

The default state of the movement actuator 326 allows the movement actuator 326 to be in the first position without a surgeon or other user needing to hold the movement actuator 326 in the first position. The pivotable portion 110 can thus remain in its inline state unless otherwise desired by the surgeon or other user. The movement actuator 326 can be configured to be manually held in any position up to and including the second position, thereby allowing the pivotable portion 110 to be pivoted at any angle up to its maximum possible angular position relative to the longitudinal axis LA. Alternatively or in addition, the movement actuator 326 can be configured to be locked in position relative to the handpiece 320 at one or more preset positions. For example, the arthroscope can include a locking mechanism configured to lock the movement actuator 326 in the second position. The locking mechanism can have any of a variety of configurations, similar to that discussed above with respect to the movement actuator 126. Regardless of the configuration of the locking mechanism configured to lock the movement actuator 326 in the second position, the movement actuator 326 can be configured to be manually held in any selected position between the first and second positions. Alternatively, the movement actuator 326 can be configured to be locked in one or more additional positions between the first and second positions, similar to that discussed above with respect to the movement actuator 126.

Figure 7:
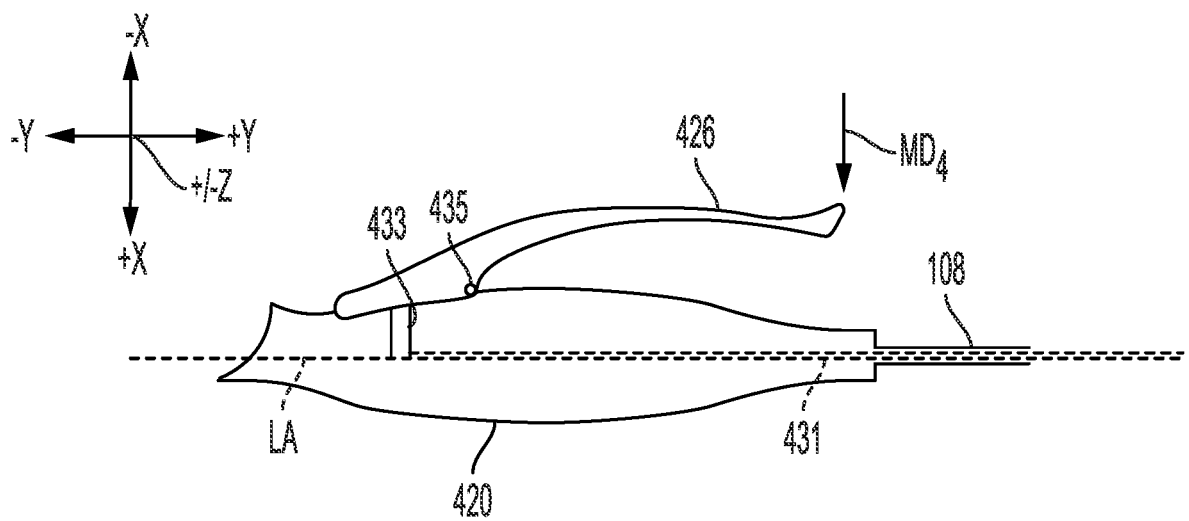
FIG. 7 is a side view of yet another implementation of the movement actuator of the arthroscopic medical implement of FIG. 1.

FIG. 7 illustrates another implementation of the movement actuator 126 as a movement actuator 426 in the form of a lever movably attached to a handpiece 420 at a pivot point 435. The handpiece 420 is configured and used similar to the handpiece 120. An actuation member 431, which in this illustrated implementation is a wire configured and used similar to the wire 131, is secured within the handpiece 420 via a mount 433, which is configured and used similar to the mount 133. The lever 426 is configured to be actuated by being pivoted at the pivot point 435, thereby changing the tension on the wire 431 to pivot the pivotable portion 110 at the pivot point 112.

FIG. 7 illustrates the movement actuator 426 in a first position, which corresponds to the pivotable portion 110 not being pivoted. With the movement actuator 426 in the first position, the wire 431 is in a non-tensioned state. With the movement actuator 426 in a second position, which corresponds to the pivotable portion 110 being pivoted, the wire 431 is in a tensioned state. As the movement actuator 426 is actuated the movement actuator 426 moves from the first position to the second position, e.g., as a user pushes the lever 426 down toward the handpiece 420 in a first movement direction $MD_4$, tension is applied to the wire 431. More particularly, as the lever 426 is pushed radially inward toward the handpiece 420 and pivots at the pivot point 435, the mount 433 secured to the lever 426 moves radially outward and thereby creates a tension in the wire 431 by pulling the wire 431 in a proximal direction. The pulling of the wire 431 causes the wire 431 to apply a proximal force to the pivotable portion 110, thereby causing the pivotable portion 110 to pivot at the pivot point 112 similar to that discussed above regarding the wire 131. Release of the lever 426 causes the tension to be released, thereby allowing the pivotable portion 110 to again pivot at the pivot point 112 and return to its inline position.

The default state of the movement actuator 426 allows the movement actuator 426 to be in the first position without a surgeon or other user needing to hold the movement actuator 426 in the first position. The pivotable portion 110 can thus remain in its inline state unless otherwise desired by the surgeon or other user. The movement actuator 426 can be configured to be manually held in any position up to and including the second position, thereby allowing the pivotable portion 110 to be pivoted at any angle up to its maximum possible angular position relative to the longitudinal axis LA. Alternatively or in addition, the movement actuator 426 can be configured to be locked in position relative to the handpiece 420 at one or more preset positions. For example, the arthroscope can include a locking mechanism configured to lock the movement actuator 426 in the second position. The locking mechanism can have any of a variety of configurations, similar to that discussed above with respect to the movement actuator 126. Regardless of the configuration of the locking mechanism configured to lock the movement actuator 426 in the second position, the movement actuator 426 can be configured to be manually held in any selected position between the first and second positions. Alternatively, the movement actuator 426 can be configured to be locked in one or more additional positions between the first and second positions, similar to that discussed above with respect to the movement actuator 126.

Referring again to FIGS. 1 and 2, the cable assembly 106 of the arthroscope 100 is configured to provide various functions to the shaft 108 through the handpiece 120. The cable assembly 106 is operably coupled to the handpiece assembly 104 to provide such functions. As in this illustrated implementation, the proximal end 122B of the handpiece 120 can include a connector 129 mateable with the cable assembly 106. The cable assembly 106 includes electrical, optical, and fluidic conduits, where each conduit is a separate cable and the handpiece 104 includes individual connectors 129 for each of the electrical, optical, and fluidic conduits. Alternatively, each of the conduits can be formed within a single cable that is configured to couple to a single connector 129 of the handpiece 120. The connector 129 can be fixedly mated with the cable assembly 106, as in this illustrated embodiment, or the connector 129 can be configured to releasably couple to the cable assembly 106.

The handpiece 120 includes at least one internal lumen to operably couple the conduits of the cable assembly 106 with the internal lumens of the shaft 108, e.g., a same number of internal lumens as the shaft 108. In this illustrated implementation, the cable assembly 106 includes a first cable 130 and a second cable 132. The first cable 130 includes a first conduit including therein electrical wire(s) configured to transfer power and data to and from any sensors of the arthroscope 100, e.g., any sensors arranged within the shaft 108 or the handpiece 120. The actuation member 131 can also be located in the first conduit. The second cable 132 includes a second conduit configured to provide irrigation fluid from a fluid source, through the handpiece 120 and one of the internal lumens 186 of the shaft 108, to a surgical site. The second cable 132 also includes a third conduit configured to provide a negative suction pressure to a surgical site through the handpiece 120 and another one of the internal lumens 188 of the shaft 108.

As mentioned above, the arthroscopic medical implement 100 can include various sensors, which can be arranged within the shaft 108 and the handpiece 120. As shown in FIG. 2, the arthroscope 100 in this illustrated implementation includes an optical sensor 140 (e.g., a photodiode, a phototransistor, a photoresistor, a fiber optic camera, or other optical sensor) configured to gather optical data, a pressure sensor 142 (e.g., a strain gauge, a gauge pressure sensor, a differential pressure sensor, or other pressure sensor) configured to gather pressure data, a temperature sensor 144 (e.g., a thermistor, a thermocoupler, a thermistor, or other temperature sensor) configured to gather temperature data, and an inertial sensor 146 (e.g., an inertial measurement unit (IMU), a gyroscope, an accelerometer, a tilt/angle switch (mercury free), or other inertial sensor) configured to gather orientation data. In other implementations, a single sensor, e.g., a single chip including a plurality of sensor capabilities, can be configured to gather data regarding two or more parameters such that one, two, or three sensors can be provided to gather optical, inertial, pressure, and temperature data. In still other implementations, one or more of the sensors 140, 142, 144, 146 can be omitted. For example, the arthroscope 100 can include the optical sensor 140 and the inertial sensor 146 but not the pressure sensor 142 and/or the temperature sensor 144.

FIG. 2 illustrates the optical sensor 140, the pressure sensor 142, the temperature sensor 144, and the inertial sensor 146 arranged within the pivotable portion 110 of the shaft 108. The sensors 140, 142, 144, 146 are shown in this implementation as being fully disposed within the pivotable portion 110, which may help protect the sensors 140, 142, 144, 146 from damage. However, at least one of the sensors 140, 142, 144, 146 can be disposed only partially within the pivotable portion 110 of the shaft 108 and/or can be disposed (fully or partially) within the shaft 108 proximal to the pivotable portion 100. The optical sensor 140, the pressure sensor 142, the temperature sensor 144, and the inertial sensor 146 being located at the pivotable portion 110 (fully or partially disposed therein) may facilitate the sensors 140, 142, 144, 146 gathering useful, accurate data at the surgical site regardless of whether or not the pivotable portion 110 is articulated relative to the longitudinal axis L at the pivot point 112, and, with the pivotable portion 110 articulated, regardless of an angle at which the pivotable portion 110 is articulated. For example, the optical sensor 140 being arranged within the pivotable portion 110 can allow for the optical sensor 140 to gather image data showing at least an area where the pivotable portion 110 is pointed at a surgical site (or where the shaft 108 is pointed at a surgical site if the pivotable portion 110 is omitted) to allow for a visual image of the surgical site to be output to a display with the shaft 108 inserted to the surgical site. For another example, the pressure and temperature sensors 142, 144 being arranged within the pivotable portion 110 can allow for the pressure and temperature sensors 142, 144 to gather pressure and temperature data, respectively, at site of interest where irrigation and/or suction is occurring instead of at some location proximal thereto where pressure and/or temperature may be different due to, e.g., its distance from the irrigation and/or suction. Pressure data may be particularly important to monitor in surgical procedures in which radiofrequency (RF) energy is being applied to tissue to, e.g., help ensure that the RF energy is being safely applied. Temperature may similarly be particularly important to monitor in surgical procedures in which RF energy is being applied to tissue.

In some implementations, the arthroscope 100 includes first and second inertial sensors 146 with the first inertial sensor 146 located at the pivotable portion 110 and the second inertial sensor 146 arranged within the handpiece 120, e.g., fully or partially disposed therein, or arranged within the shaft 108, e.g., fully or partially disposed therein, proximal to the pivotable portion 110. Providing a second inertial sensor 146 proximal to the pivotable portion 110, regardless of whether the second inertial sensor 146 is located at the shaft 108 or at the handpiece 120, may facilitate determination of the arthroscope's orientation by gathering orientation data at the pivotable portion 110, which may be pivoted at the pivot point 112, and at the shaft 108 (proximal to the pivot point 112) or handpiece 120, which do not pivot relative to the longitudinal axis LA.

The arthroscope 100 includes a lens 114 disposed distal to the optical sensor 140. The lens 114 is configured to protect the optical sensor 140 from damage by preventing liquid and/or solid matter at a surgical site from directly contacting the optical sensor 140. The lens 114 can, in some implementations, provide an optical feature such as magnification to enhance optical data gathered by the optical sensor 140.

The arthroscope 100 includes a prism 115 disposed distal to the lens 114 and thus disposed distal to the optical sensor 140. The prism 115 is configured to provide a greater angle of view for the optical sensor 140 than would be achievable without the prism 115. The prism 115 is at the pivotable portion 110 of the shaft 108, which allows the prism 115 to pivot with the pivotable portion 110 and the optical sensor 140 and the lens 114 attached thereto. In an exemplary implementation, the prism 115 is angled in the range of about 30° to about 70°. Arthroscopic hip surgery traditionally involves use of two scopes or other image devices, one with a fixed 30° viewing angle and the other with a fixed 70° viewing angle. The prism 115 and the pivotable portion 110 allows the arthroscope 100 to provide a 30° viewing angle and a 70° viewing angle such that one device can be used instead of two devices such that space may be freed at the surgical site for other instruments and/or to provide better visualization opportunities and/or such that a number of incisions made in the patient may be reduced since two incisions need not be made for two different devices. In some implementations, the prism 115 is omitted, but the angular range of about 30° to about 70° may still be achieved with the arthroscope 100 via pivoting of the pivotable portion 110.

Exemplary implementations of the optical sensor 140 include the OMV7695 sensor, the OC01A10 sensor, and the OH0A10 sensor available from OmniVision Technologies, Inc. of Santa Clara, CA, although other optical sensors can be used.

The handpiece 120 can include one or more image control actuators (e.g., button(s), lever(s), etc.) configured to configured one or more functions of the optical sensor 140. For example, the handpiece 120 can include an image control actuator configured to be actuated to cause the optical sensor 140 to gather a still image on demand, e.g., to trigger the control unit 160 to cause the optical sensor 140 to gather an image and transit the gathered data to the control unit 160. For another example, the handpiece 120 can include an image control actuator configured to be actuated to turn the optical sensor's image data gathering on and off, e.g., to trigger the control unit 160 to cause the optical sensor 140 to start gathering video images or to cause the optical sensor 140 to stop gathering video images.

In an exemplary implementation, the movement actuator 126 is configured to indicate an angular orientation of the prism 115 when the pivotable portion 110 of the arthroscope 100 is not pivoted (or if the pivotable portion 110 is omitted). As discussed above, the movement actuator 126 is arranged on the handpiece 120. A radial location of the movement actuator 126 around a circumference of the handpiece 120 corresponds to a direction in which the prism 115 is angled when the pivotable portion 110 of the arthroscope 100 is not pivoted (or if the pivotable portion 110 is omitted). A surgeon or other user of the arthroscope 100 may thus be able to look at the movement actuator 126 located outside of a patient's body to know an orientation of the prism 115 located within the patient's body, which may help the surgeon or other user adjust rotational position of the arthroscope 100 and/or pivoted position of the pivotable portion 110.

Figure 8:
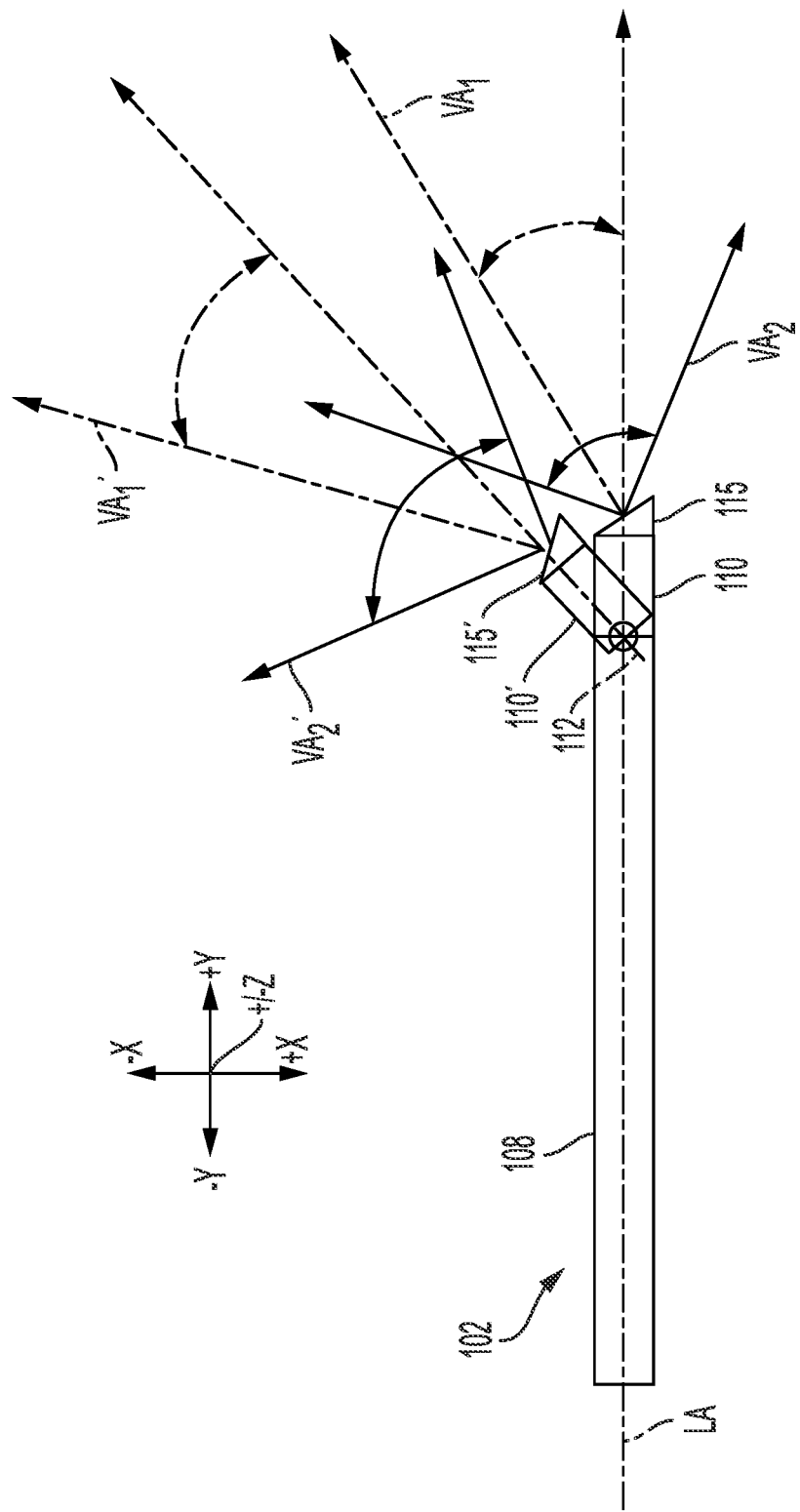
FIG. 8 is a schematic side view of one implementation of a longitudinal shaft and a pivotable tip of the arthroscopic medical implement of FIG. 1.

FIG. 8 illustrates an example of the pivoting of the pivotable portion 110 of the arthroscopic medical implement 100. The pivotable portion 110 is shown in FIG. 8 in an inline position, in which the pivotable portion 110 is not pivoted and is labeled with reference numeral 110, and shown in FIG. 8 in a pivoted position, in which the pivotable portion 110 is pivoted at the pivot point 112 and is labeled with reference numeral 110'. Only one pivoted position is shown in FIG. 8, but as discussed herein, numerous pivoted positions of the pivotable portion 110 are possible.

FIG. 8 also illustrates viewing angles of the optical sensor 140 corresponding to the pivotable portion 110 in the inline position (prism 115 labeled with reference numeral 115) and in the pivoted position (prism 115 labeled with reference numeral 115'). With the pivotable portion 110 in the inline position, the optical sensor 140 has a viewing angle $VA_2$, which in this illustrated implementation is about 90° but can be another angle given the optical sensor's particular configuration. The prism 115 allows the viewing angle $VA_2$ to be greater than possible without the prism 115. Without the prism 115, the viewing angle of the optical sensor 140 would be a smaller viewing angle $VA_1$, which in this illustrated implementation is about 30° but can be another angle given the optical sensor's particular configuration. The prism 115 is therefore configured to increase the viewing angle of the optical sensor 140. In an exemplary implementation, the prism 115 is angled in a range of about 30° to about 70°, which increases the optical sensor's viewing angle correspondingly. The prism 115 in this illustrated implementation is angled at about 60° so as to increase the optical sensor's viewing angle by about 60°, e.g., from about 30° to about 90°.

With the pivotable portion 110' in the pivoted position, the optical sensor 140 still has the viewing angle $VA_2$' of about 90°, increased from the smaller viewing angle $VA_1$' of about 30° that would be achieved without the prism 115'. By arranging the prism 115 distal to and over the optical sensor 140, in combination with the pivotable portion 110 being pivoted, the optical sensor 140 can gather images at an angle of about 90° from the longitudinal axis LA, and in some implementations, greater than about 90°. For example, as in this illustrated implementation with the pivotable portion 110' in the pivoted position, the viewing angle $VA_2$' of about 90° allows the optical sensor 140 to gather images at an angle greater than about 90° from the longitudinal axis LA.

Referring again to FIGS. 1 and 2, the optical sensor 140, the pressure sensor 142, the temperature sensor 144, and the inertial sensor 146 are operably coupled to a control unit 160 via an electrical connector in the form of a cable 148. The cable 148 passes through one of the internal lumens of the shaft 108 and through the handpiece 120 to the first cable 130 of the cable assembly 106 to allow for power and data transfer as discussed above.

As shown in FIG. 2, each of the cables 130, 132 is operatively coupled to a control unit 160. The control unit 160 includes a processor 162, a memory 164, a storage device 166, and a system bus 168 that interconnects the processor 162, the memory 164, and the storage device 166 of the control unit 160. The processor 162 is configured to execute instructions stored in the memory 164 and/or on the storage device 166 to provide control functionality of the control unit 160. In some implementations, the processor 162 is a single-threaded processor. In other implementations, the processor 162 is a multi-threaded processor. The memory 164 is configured to store information and is a computer-readable medium, e.g., a volatile memory unit or a non-volatile memory unit. The storage device 166 is configured to provide mass storage for the control unit 160 and is a computer-readable medium, e.g., a floppy disk device, a hard disk device, an optical disk device, a tape device, non-volatile solid state memory, etc. In an exemplary implementation, the memory 164 is configured to store pre-programmed instructions configured to be executed by the processor 162, and the storage device 166 is configured to store gathered sensor data. As discussed herein and as shown by arrows on the first cable 130 and the electrical connector 148 in FIG. 2, data gathered by the sensors 140, 142, 144, 146 can be provided to the control unit 160, which the processor 162 can cause to be stored in the storage device 166. The control unit 160 can also be configured to provide instructions to one or more of the sensors 140, 142, 144, 146 via the cables 130, 148, such as an instruction for one or more of the sensors 140, 142, 144, 146 to gather data and provide the gathered data to the control unit 160.

The control unit 160 is operably coupled to a display unit 172, e.g., a CRT screen, an LCD screen, a touchscreen, etc., configured to show information thereon. The display unit 172 is operably coupled to the control unit's processor 162 via a cable 174 to allow the processor 162 and the display unit 172 to communicate with one another. An arrow on the cable 174 in FIG. 2 shows data flow only from the control unit 160 to the display unit 172, but the display unit 172 can be configured to transmit data to the control unit 160, e.g., error information, user inputs input by a user via a user interface (e.g., button(s), touchscreen, etc.) of the display unit 172, etc. The control unit 160, e.g., using the processor 162, is configured to provide display instructions and data to display to the display unit 172, such as instructions to display optical image from the optical sensor 140 that the control unit 160 provides the display unit 172 via the cable 174, instructions to display pressure information gathered by the pressure sensor 142 that the control unit 160 provides the display unit 172 via the cable 174, instructions to display temperature information gathered by the temperature sensor 144 that the control unit 160 provides the display unit 172 via the cable 174, instructions to display orientation information from the inertial sensor 146 that the control unit 160 provides the display unit 172 via the cable 174, etc. Instead of a wired connection using the cable 174, the control unit 160 can additionally or alternatively be configured to communicate wirelessly with the display unit 172. In some implementations, the display unit 172 and the control unit 160 can be part of a same computer system, e.g., a single electronic tablet, a single laptop computer, etc.

The control unit 160, e.g., the processor 162 thereof, is configured to determine an orientation of the optical sensor 140 using orientation data gathered by the inertial sensor 146. In an exemplary implementation, the orientation data measured by the inertial sensor 146 includes angular orientation data and axis orientation data. Gathering angular orientation data and axis orientation data may facilitate accurate determination by the control unit 160 of the orientation of the optical sensor 140 by allowing determination of the optical sensor's rotation, e.g., whether the optical sensor 140 is rotating about the X axis, the Y axis, or the Z axis, and the optical sensor's translation, e.g., whether the optical sensor 140 is translating along the X axis, the Y axis, or the Z axis.

The control unit 160 is configured to receive optical image data from the optical sensor 140 and orientation data from the inertial sensor 146, as discussed above, and can be configured to modify the optical image data using the orientation data. The modification includes rotating the optical image output to the display unit 172 in order to maintain the displayed optical image in a desired orientation during and after rotation of the handpiece 120, e.g., during and after the handpiece 120 is rotated about the longitudinal axis LA. In an exemplary implementation, the desired orientation is upright but can be another orientation, such as sideways.

As shown in FIG. 2, the plurality of input actuators 124 are operably coupled to the control unit 160 via a cable 150, which is operably coupled to the first cable 130. The connection between the input actuators 124 and the control unit 160 allows for a surgeon or other user to provide irrigation fluid to the surgical site by actuating a selected one of the plurality of input actuators 124, e.g., a one of the input actuator 124 most easily accessible to the user given the user's current hand position relative to the handpiece 120 and thus relative to the input actuators 124. Actuation of any one of the input actuators 124 is configured to cause an input actuation signal to be transmitted from the actuated input actuator 124 along the cable 150 and then along the first cable 130 to the control unit 160, e.g., to the processor 162 thereof. In response to the control unit's receipt of the input actuation signal, the control unit 160, e.g., the processor 162, is configured to cause an activation signal to be transmitted a pump 134 along a third cable 170 (or instead of along the third cable 170, along a wireless connection between the pump 134 and the control unit 160). The pump 134 is fluidly coupled to an external fluid source 136 that is external to the arthroscope 100. In response to receipt of the activation signal, the pump 134 is configured to pump irrigation fluid from the fluid source 136 through the second cable 132 to the arthroscope 100, and in particular to the handpiece 120 and then through one of the internal lumens of the shaft 108 and out of the shaft 108 to a surgical site. The pump 134 is external to the control unit 160 in the illustrated implementation of FIG. 2 but can be integrated with the control unit 160.

The pump 134 is configured to continue pumping fluid from the fluid source 136 to the arthroscope 100 until the pump 134 receives a stop signal from the control unit 160. Fluid can thus be continuously provided to the surgical site. The control unit 160 is configured to cause the stop signal to be transmitted to the pump 134 in response to surgeon/user release of the actuated input actuator 124. The surgeon's/user's release of the actuated input actuator 124 stops the input signal from being transmitted therefrom to the control unit 160 and/or causes a deactivation signal to be transmitted from the de-actuated input actuator 124 to the control unknit 160, thereby triggering the control unit 160 to transmit the stop signal to the pump 134. For example, when the input actuator 124 is in the form of a button, the surgeon or other user can press down on the button to cause irrigation fluid flow and can release the pressed-down button to cause the irrigation fluid flow to stop. For another example, when the input actuator 124 is in the form of a lever, the surgeon or other user can move the lever from a first position to a second position to cause irrigation fluid flow and can move the lever from the second position back to the first position to cause the irrigation fluid flow to stop.

In other implementations, a first actuation of a selected one of the input actuators 124 is configured to trigger the control unit 160 to transmit the activation signal to the pump 134, and a second actuation of a selected one of the input actuators 124 (same or different as the input actuator 124 actuated in the first actuation) is configured to trigger the control unit 160 to transmit the stop signal to the pump 134. The surgeon or other user thus need not continuously actuate, e.g., hold a button, apply pressure to a lever, etc.) for fluid to be continuously pumped to a surgical site, which may reduce hand fatigue and/or ease rotation of the arthroscope 100 while fluid is being pumped to a surgical site.

Figure 9:
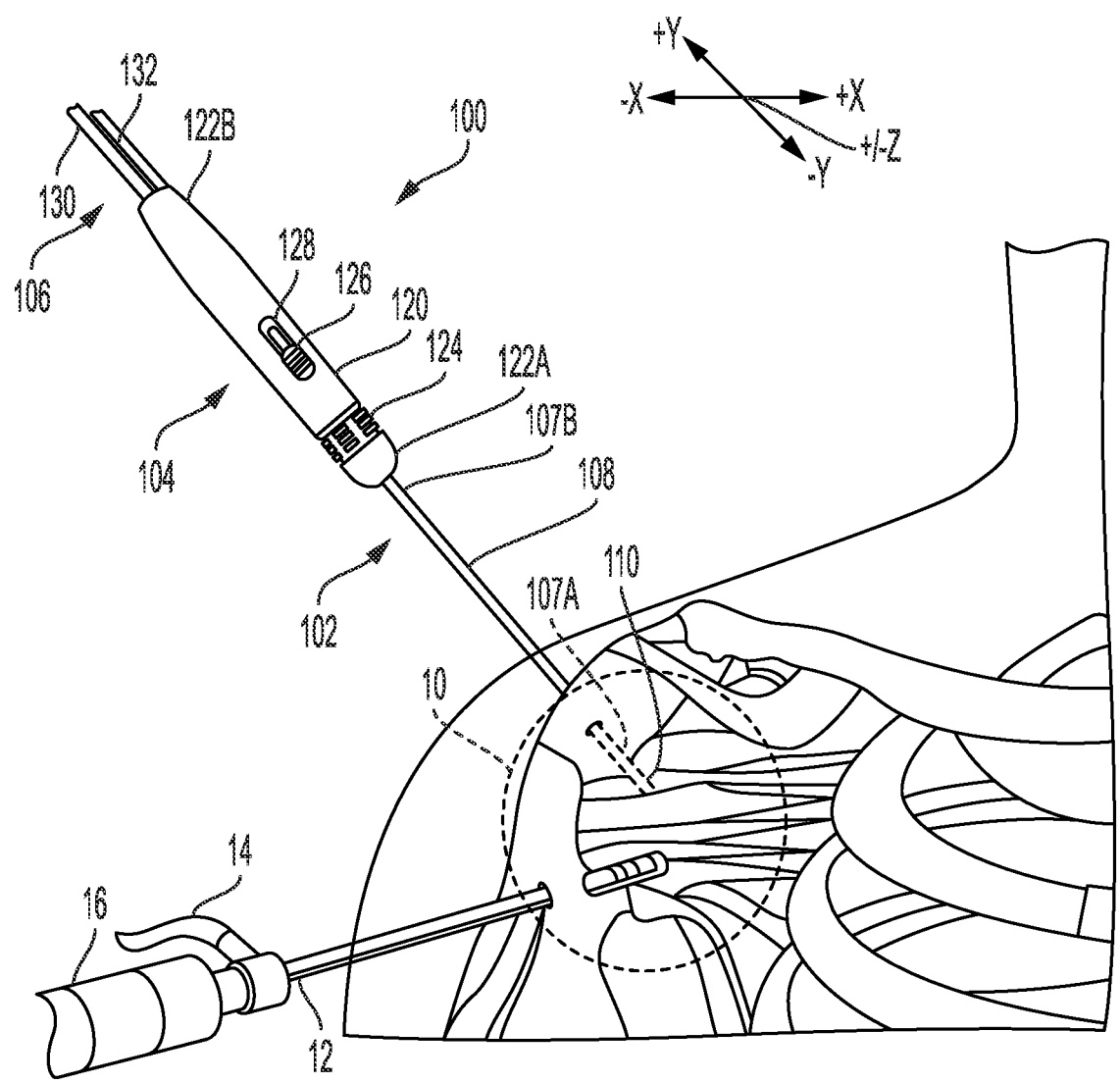
FIG. 9 is a perspective view of the arthroscopic medical implement of FIG. 1 inserted within a surgical site.

FIG. 9 illustrates the arthroscopic medical implement 100 inserted into a patient and to a surgical site 10. The surgical site 10 is at a shoulder of the patient in this illustrated implementation but can be at other locations such as the hip or the knee. As shown in FIG. 9, the shaft 108 is inserted arthroscopically through an incision in skin of the patient and positioned with a distal portion of the medical implement 100 at the surgical site 10. The optical sensor 140 is arranged at the pivotable portion 110 of the shaft 108, allowing a surgeon to observe the surgical site 10 on the display unit 172. In order to observe a different portion of the surgical site 10, the surgeon or other user handling the arthroscope 100 can tilt the shaft 108 within the incision, the surgeon or other user handling the arthroscope 100 can rotate the handpiece 120 and the shaft 108 (including the pivotable portion 110) about the longitudinal axis LA, and/or the surgeon or other user handling the arthroscope 100 can pivot the pivotable portion 110 by actuating the movement actuator 126.

As shown in FIG. 9, a secondary tool 12 can be inserted into the patient and to the surgical site 10. In this illustrated implementation, the secondary tool 12 is a shaver, but other secondary tools can be used such as a second arthroscope. The shaver 12 includes a suction conduit 14 configured to remove therethrough material such as shaved-off tissue, shaved-off bone, and irrigation fluid from the surgical site 10. The same user can simultaneously handle the arthroscope 100 and the secondary tool 12 by holding the arthroscope 100, e.g., the handpiece 120 thereof, with one hand and holding the secondary tool 12, e.g., a handle 16 thereof, with another hand.

Figure 10:
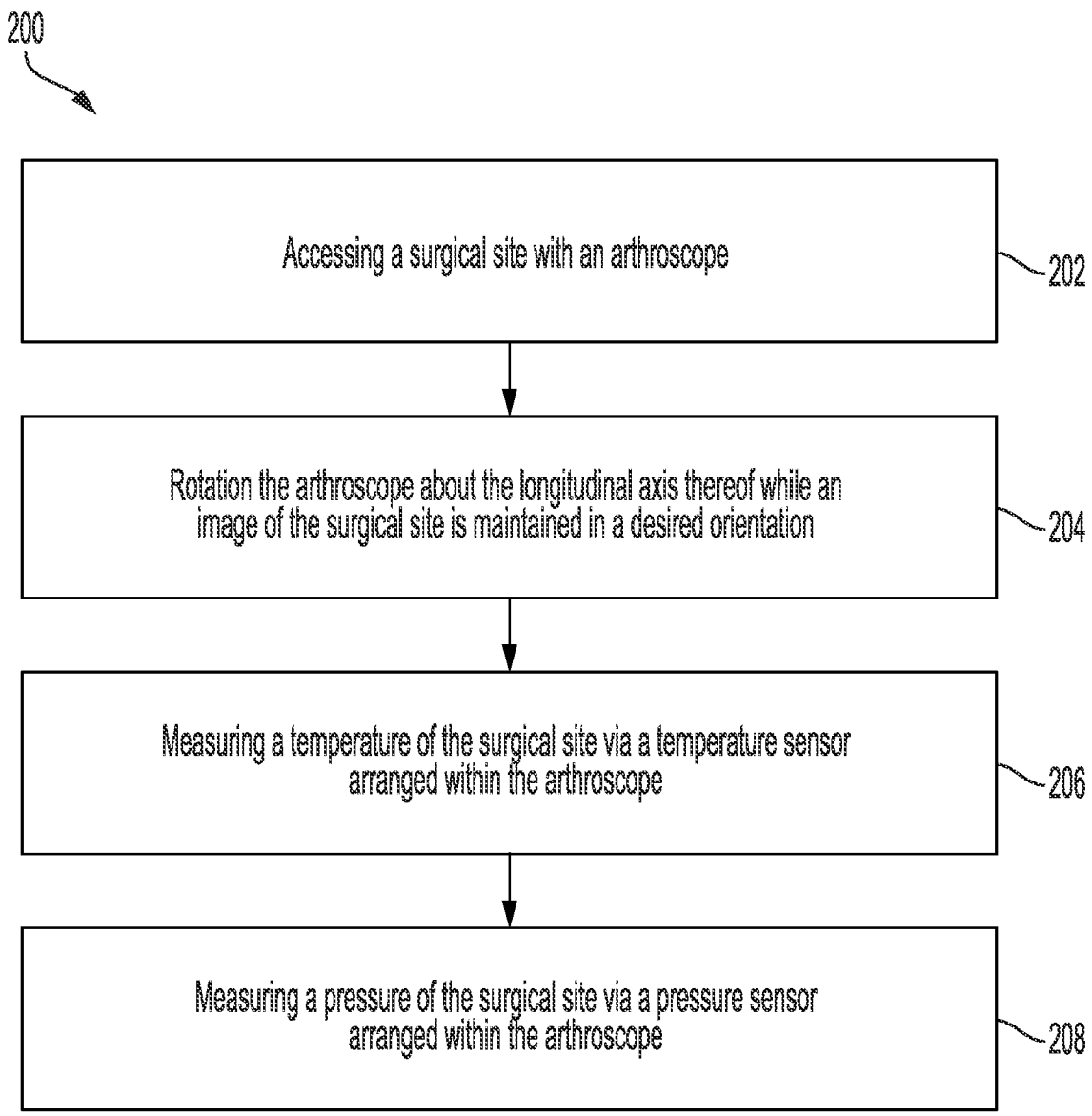
FIG. 10 is one implementation of a method of operation of the arthroscopic medical implement of FIG. 1 within a surgical site.

FIG. 10 illustrates one exemplary method 200 of operating an arthroscopic medical implement. The method 200 is described with respect to the arthroscopic medical implement 100 of FIGS. 1 and 2, but other implementations of arthroscopic medical implements described herein can be similarly used. In general, the method 200 can be used in performing an arthroscopy procedure in which a surgical site is accessed with the arthroscopic medical implement 100, optical image data outputted from the optical sensor 140 is modified based on the orientation data from the inertial sensor 146, and the modified optical image is output to the display unit 172 such that the display unit 172 continuously shows the surgical site in a desired orientation.

The method 200 includes accessing 202 the surgical site with the arthroscopic medical implement 100 by a user such as a surgeon inserting the distal end 107A of the shaft 108 into a patient and to a surgical site. The method 200 also includes the user rotating 204 the handpiece 120 about the longitudinal axis LA, which also rotates the shaft 108 (including the pivotable portion 110 at which the sensors 140, 142, 144, 146 are located), while an image of the surgical site shown on the display unit 172 is maintained 204 in a desired orientation. In order for the image to remain in the desired orientation, the optical image data received at the control unit 160 from the optical sensor 140 is modified by the control unit 160 using orientation data provided to the control unit 160 from the inertial sensor 146. For example, when the optical sensor 140 is activated initially, the control unit 160 uses orientation data from the inertial sensor 146 to determine a zero rotation point, where the optical sensor 140 is oriented upright. As the handpiece 120 is rotated along the longitudinal axis LA, the control unit 160 can measure an angular position of the optical sensor 140 from the zero rotation point based on gathered orientation data. Prior to outputting an image of the surgical site to the display 172, the control unit 160 modifies the image by rotating the image the same angular amount about the longitudinal axis LA that the angular position of the optical sensor 140 is from the zero rotation point, as indicated by the orientation data gathered by the inertial sensor 146. The control unit's modifying of the optical image data occurs in real time with the gathering of the optical image data, as the optical sensor 140 is configured to transmit gathered optical image data to the control unit 160 in real time with the gathering. The inertial sensor 146 is also configured to transmit its gathered orientation data to the control unit 160 in real time. Thus, there is little to no delay between rotation of the handpiece 120 and shaft 108 and the output of the modified image to the display unit 172.

The pressure and temperature sensors 142, 144 can also be configured to transmit their respectively gathered pressure and temperature data in real time with its gathering so pressure and temperature information can be shown on the display unit 172 in real time to help provide accurate, up-to-date information to the surgeon and/or other medical personnel monitoring information shown on the display unit 172.

Figure 11A:
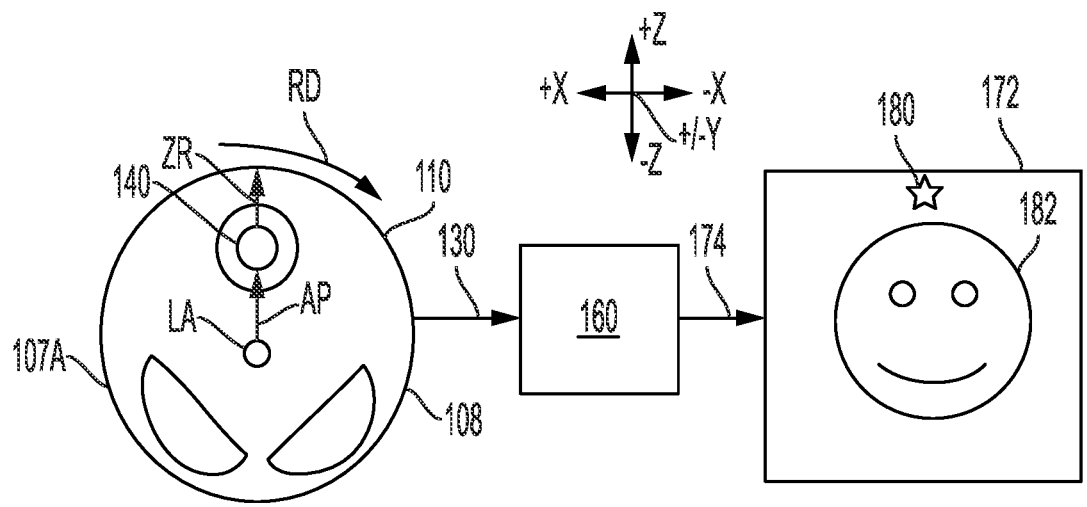
FIG. 11A is a schematic view of the arthroscopic medical implement of FIG. 1 in a first angular position.
Figure 11B:
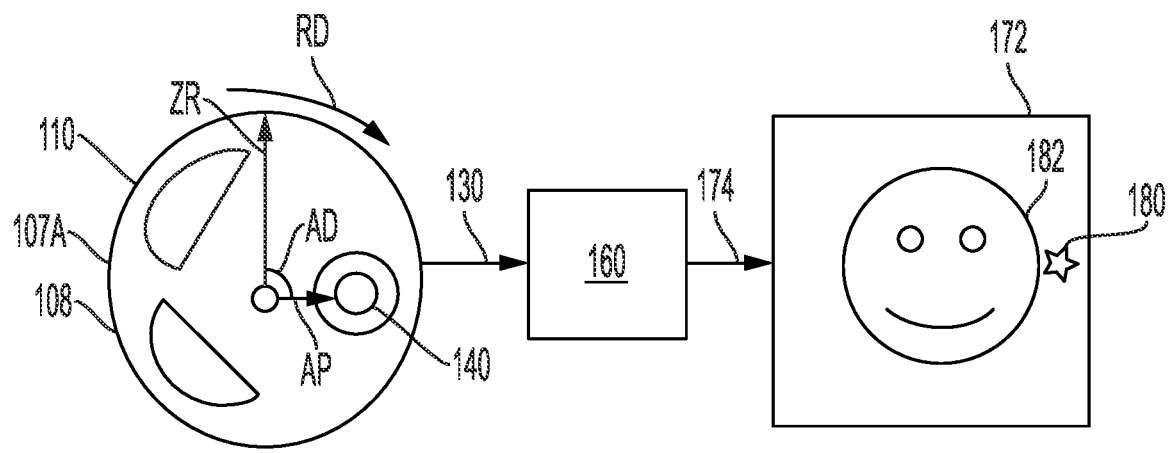
FIG. 11B is a schematic view of the arthroscopic medical implement of FIG. 1 in a second angular position.
Figure 11C:
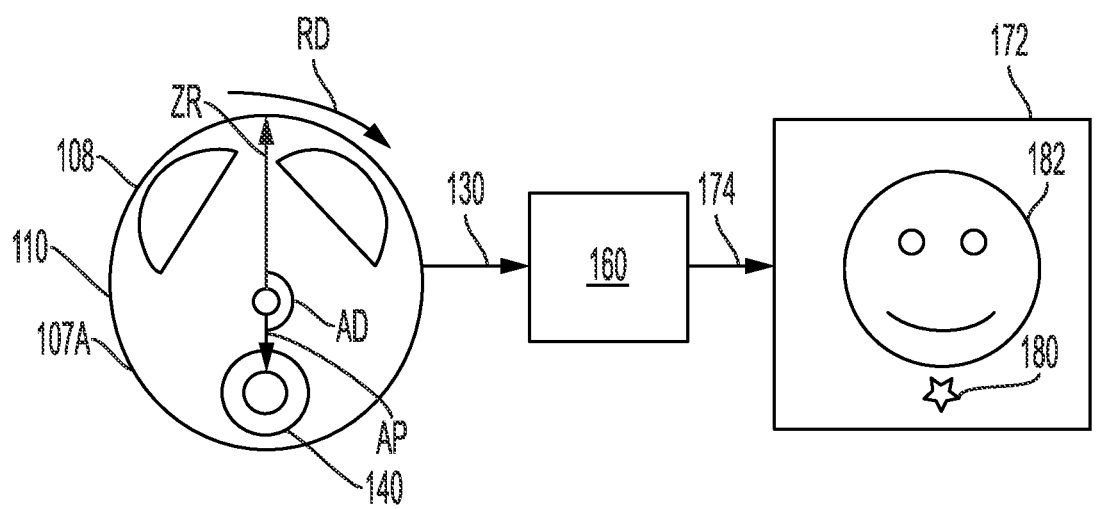
FIG. 11C is a schematic view of the arthroscopic medical implement of FIG. 1 in a third angular position.

FIGS. 11A-11C illustrate one implementation of the handpiece's rotation 204 and an image 182 being maintained 204 in a desired orientation on the display unit 172. The image 182 is a smiley face in FIGS. 5A-5C for ease of illustration and understanding but would in use be an image of the surgical site 10.

As shown in FIG. 11A, an angular position AP of the optical sensor 140 is arranged at a zero rotation point ZR, e.g., the optical sensor angular position AP and the zero rotation point ZR are aligned. This relative positioning corresponds to the initial activation of the optical sensor 140, e.g., when power is first provided to the optical sensor 140 during the surgical procedure and/or when the control unit 160 causes the optical sensor 140 to first begin gathering optical data during the surgical procedure. When the angular position AP of the optical sensor 140 aligns with the zero rotation point ZR, the control unit 160 does not need to modify the gathered optical image because the image data is already at a desired orientation as gathered. The zero rotation point ZR is depicted as a reference image 180 on the display unit 172 that is also showing thereon the optical image 182. In an exemplary implementation, the image 180 is displayed on the display unit 172 to indicate to a surgeon and/or other medical personnel how rotated the optical sensor 140 is from the zero rotation point ZR. However, in some implementations, the reference image 180 is not displayed on the display unit 172, which may help reduce clutter on the display unit 172. The reference image 180 is a star in this illustrated implementation but can have other forms, such as a horizon indicator (artificial horizon) similar to that on a flight instrument, a circle, a triangle, text (e.g., "zero," "zero point," "reference," "ZR," etc.), a square, a house (home) icon, etc. The desired orientation in this illustrated implementation is upright, as indicated by the smiley face being oriented upright with eyes at the top and mouth at the bottom, although other orientations are possible, such as sideways to the right, e.g., eyes at the right and mouth at the left, or sideways to the left, e.g., eyes at the left and mouth at the right.

As the handpiece 120 is rotated in a rotation direction RD about the longitudinal axis LA from the position of FIG. 11A, the optical sensor 140 also rotates about the longitudinal axis LA. The rotation direction RD is clockwise in the illustrated implementation of FIG. 11A, but the rotation direction RD can be counterclockwise. Rotating the optical sensor 140 in the rotation direction RD causes the angular position AP of the optical sensor 140 to no longer be aligned with the zero rotation position ZR, thereby resulting in an angular displacement AD of the optical sensor 140 from the zero rotation position ZR, as shown in FIG. 11B. The control unit 160 is informed of the angular displacement AD by the orientation data gathered by the inertial sensor 146 and transmitted to the control unit 160. FIG. 11B shows the angular displacement AD as being about 90°, e.g., an angle of about 90° between the zero rotation point ZR and the angular position AP of the optical sensor 140, but other angular displacements AD are possible. The control unit 160 modifies the optical image data transmitted from the optical sensor 140 to the control unit 160 based on the orientation data from the inertial sensor 146, e.g., based on the angular displacement AD. FIG. 11B shows the modified image 182 and the reference image 180 on the display unit 172. Even though the zero rotation point ZR represented by the reference image 180 is rotated about 90° on the display unit 172 from its initial position shown in FIG. 11A, the image 182 remains in the desired orientation as compared to the image 182 illustrated in FIG. 11A, where the angular displacement AD is 0°.

As the handpiece 120 is further rotated in the rotation direction RD about the longitudinal axis LA from the position of FIG. 11B, the control unit 160 modifies the image 182 for display on the display unit 172 accordingly. FIG. 11C shows the angular displacement AD as being about 180°, e.g., an angle of about 180° between the zero rotation point ZR and the angular position AP of the optical sensor 140, but other angular displacements AD are possible as mentioned above. Even though the zero rotation point ZR represented by the reference image 180 is rotated about 180° on the display unit 172 from its initial position shown in FIG. 11A, and rotated about 90° on the display unit 172 from its first intermediate position shown in FIG. 11B, the image 182 in its second intermediate position shown in FIG. 11C remains in the desired orientation as compared to the image 182 illustrated in FIGS. 11A and 11B.

The control unit 160 is configured to continuously update the display unit 172 as the arthroscope 100 is rotated so the image 182 remains in the desired orientation and the reference image 180 (if present on the display unit 172) is positioned accurately relative to the image 182. The control unit 160 is also configured to continuously update the display unit 172 in other ways while maintaining the image 182 in the desired orientation on the display unit 172 and the reference image 180 on the display unit 172 in the same relative position to the image 182, such as by updating the image 182 if zoomed in, if zoomed out, as different element(s) move in and out of the optical sensor's field of view, etc.

Referring again to FIG. 10, the method 200 also includes measuring 206 a temperature of the surgical site 10 using the temperature sensor 144 of the arthroscope 100 and measuring 208 a pressure of the surgical site 10 using the pressure sensor 142 of the arthroscope 100. The temperature and pressure measurements are transmitted to the control unit 160, as discussed above, and the control unit can output pressure and temperature information to the display unit 172 for real time display thereon.

The method 200 illustrated in FIG. 10 shows the arthroscope's rotation 202 occurring before the temperature measurement 204 and the temperature measurement 206 occurring before the pressure measurement 206, but the rotation 202, temperature measurement 204, and pressure measurement 206 can occur in other orders, can occur with the same action (e.g., rotation 202, temperature measurement 204, or pressure measurement 206) occurring more than one time in a row before either of the other two actions 202, 204, 206 occur, and can each occur multiple times throughout performance of the surgical procedure.

Accessing 202 the surgical site with the arthroscopic medical implement 100 can include use of an insertion tool. In general, the insertion tool may facilitate safe and easy guiding of the arthroscopic medical implement 100 to the surgical site. The insertion tool can have a variety of configurations.

Figure 12A:
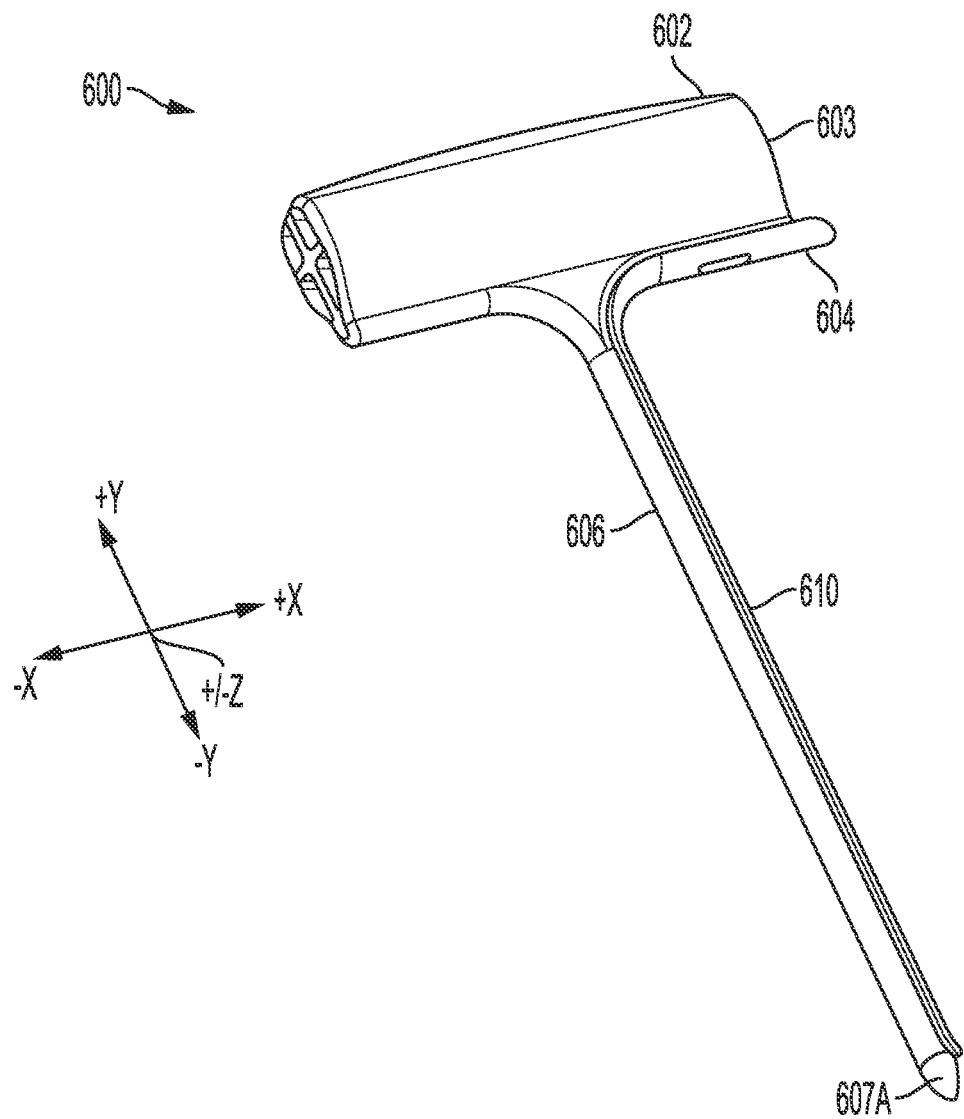
FIG. 12A is a perspective view of one implementation of an insertion tool.
Figure 12B:
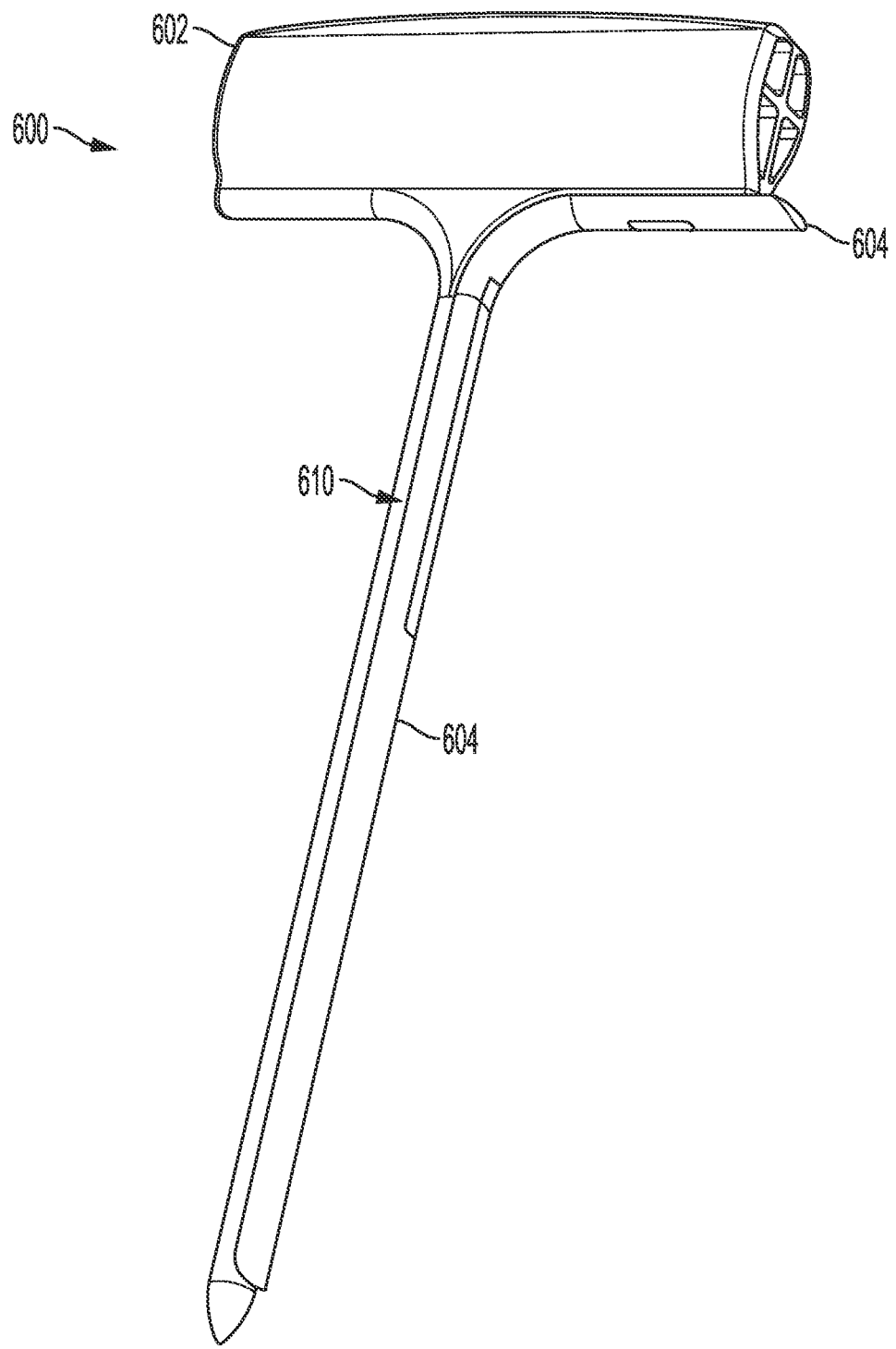
FIG. 12B is another perspective view of the insertion tool of FIG. 12A.

FIGS. 12A and 12B illustrate one implementation of an insertion tool 600 configured to facilitate insertion of an arthroscope, e.g., the arthroscopic medical implement 100 or other arthroscopic medical implement described herein, into a surgical site. The insertion tool 600 includes an obturator 602 and a guide member 604 (also referred to herein as a "sled") releasably secured to the obturator 602. The obturator 602 includes a handle 603 and an elongate shaft 606 that extends distally from the handle 603. The elongate shaft 606 includes a tapered distal end 607A. The handle 603 is configured to receive an insertion force applied thereto in a distal direction, e.g., by hand or by a tool pushing distally against the handle 603, to insert the insertion tool 600 into a patient's body and to a surgical site therein. The tapered shape of the shaft's distal end 607A is configured to aid in the insertion of the insertion tool 600 into the patient's body by widening a pre-formed incision in the patient's skin, e.g., cut in the skin with a scalpel or other cutting tool, as the insertion tool 600 is advanced through the incision. In other implementations, the tapered distal end 607A can include a sharp edge configured to form the incision in the patient's skin and then widen the incision as the insertion tool 600 is advanced through the incision.

The sled 604 includes a guide channel 610 that extends along a length thereof. The guide channel 610 is along an exterior surface of the sled 604. The obturator 602 is configured to be releasably seated in the guide channel 610 to be releasably secured to the sled 604. The obturator 602 and the guide channel 610 have sizes and shapes such that the obturator 602, including the elongate shaft 606 and the handle 603, is configured to be seated in the guide channel 610 with a friction fit. The friction fit between at least the sled 604 and the elongate shaft 606 may help ensure that the obturator 602 and the sled 604 remain mated together during insertion of the insertion tool 600 into a body of a patient and to a surgical site within the patient. The handle 603 being configured to be seated in the guide channel 610 so as to be positioned proximal to the sled 604, as shown in FIGS. 12A and 12B, may help ensure that the sled 604 and the obturator 602 stay in a fixed positon relative to one another as the insertion tool 600 is advanced distally into a patient's body and to a surgical site. The obturator 602 is configured to be released from the sled 604 by pulling proximally on the obturator 602, e.g., by the handle 603, to slide the obturator 602 out of the guide channel 610.

In one implementation of a method of using the insertion tool 600 with an arthroscope, such as the arthroscope 100 or other arthroscopes described herein, once the insertion tool 600 is advanced to a desired position at a surgical site, the obturator 602 is released from the guide member 604. The obturator 602 is removed from the surgical site and from the patient's body, e.g., by pulling the handle 603 proximally to move the obturator 602 through and out of the incision. The elongate shaft 606 slides proximally within the guide channel 610 during the obturator's removal. The guide member 604 remains positioned in the incision and at the surgical site after the obturator 602 has been released from the guide channel 610 and removed from the surgical site and the patient's body. The guide member 604 has a length that, with the guide member 604 extending through the incision to the surgical site, allows a proximal portion of the guide member 604 to be located outside of the patient's body and a distal portion of the guide member 604 to be located within the patient's body. The shaft 108 of the arthroscopic medical implement 100 or other arthroscope described herein can then be seated in and slid distally within the guide channel 610 to access the surgical site. The arthroscope 100 can later be released from the guide member 604 similar to that discussed above regarding release of the insertion member 602 from the guide channel 610. The arthroscope 100 and/or one or more other tools can be seated and slid in the guide channel 610 to access the surgical site. The guide member 604 allows for the removal and reinsertion of the arthroscope 100 and/or other tool without the need to make a new incision since the guide member 604 will keep the incision partially open.

As discussed above, in an exemplary implementation, a connector, whether a single connector or a plurality of connectors, is configured to make all electrical, optical, and fluidic connections for an arthroscope by connecting to a plurality of cables that are configured to provide electrical, optical, and fluidic functionality. The plurality of cables are also configured to operably couple to a control unit. The connector is at a distal end of the plurality of cables, and the control unit is at a proximal end of the plurality of cables. FIGS. 1 and 2 illustrate one such implementation, in which the connector 129 is at a distal end of the cable assembly 106 that includes the first and second cables 130, 132, and the control unit 160 is at a proximal end of the cable assembly 106. FIGS. 1 and 2 illustrate the connector 129 at the distal end of the cable assembly 106, and FIG. 2 illustrates the proximal end of the cable assembly 106 operably coupled to the control unit 160.

Figure 13:
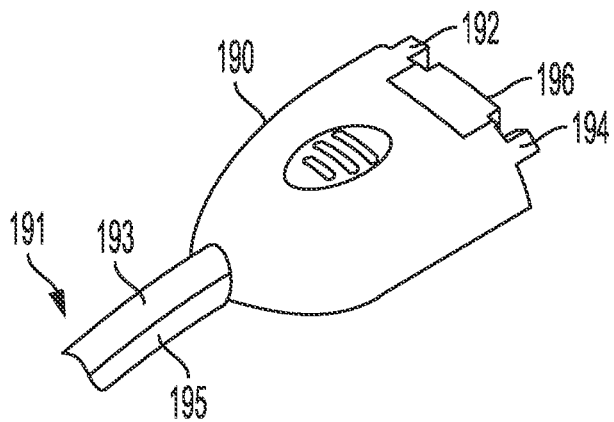
FIG. 13 is a perspective view of one implementation of a cable connector and a cable assembly.

The plurality of cables can be configured to operably couple to a control unit in a variety of ways. FIG. 13 illustrates one implementation of a cable connector 190 configured to operably couple to a control unit. The cable connector 190 is at the proximal end of a cable assembly 191 and is configured to operably couple to a control unit, e.g., a control unit 700 (discussed further below) or other implementation of a control unit described herein. The cable assembly 191 is generally configured and used similar to the cable assembly 106 of FIGS. 1 and 2. The cable assembly 191 in this illustrated implementation includes a first cable 193 and a second cable 195. The first cable 193 includes a first conduit including electrical wire(s) and is configured and used similar to that discussed above regarding the first cable 130 of the cable assembly 106. The second cable 195 includes a second conduit configured to provide irrigation fluid from a fluid source and is configured and used similar to that discussed above regarding the second conduit of the second cable 132 of the cable assembly 106. In this illustrated implementation, the second cable 195 does not include a third conduit for suctioning.

Figure 14:
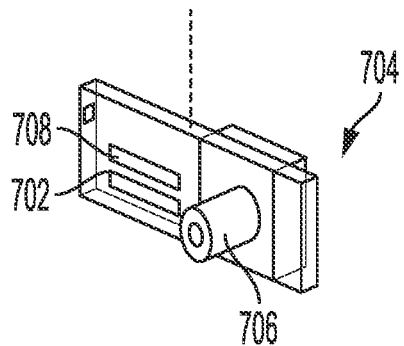
FIG. 14 is a perspective view of a portion of one implementation of a control unit.

The cable connector 190 includes an electrical connector 192 and a fluid connector 194. The electrical connector 192 is configured to operably couple to a corresponding electrical connector of a control unit, and the fluid connector 194 is configured to operably couple to a corresponding fluid connector of the control unit. FIG. 14 illustrates one implementation of such control unit electrical and fluid connectors. The electrical connector 192 is configured to operably couple to a corresponding electrical connector 702 at a cable port 704 of a control unit 700, discussed further below. With the electrical connector 192 operably coupled to the control unit's electrical connector 702, the control unit 700 can provide power to the arthroscope 100 via the first cable 130, and data can be communicated via the first cable 191 from the arthroscope 100 to the control unit 700 and/or from the control unit 700 to the arthroscope 100. The fluid connector 194 is configured to operably couple to a corresponding fluid connector 706 at the cable port 704 of the control unit 700. With the fluid connector 194 operably coupled to the control unit's fluid connector 706, the control unit 700 can provide fluid irrigation via the second cable 193.

The cable connector 190 also includes a securing member 196 configured to facilitate a secure, releasable connection of the cable connector 190 to the control unit 700. As in the implementation of FIG. 14, the control unit 700 can include a corresponding securing member 708 at the cable port 704 that is configured to securely, releasably engage the securing member 196. The securing member 196, 708 of one of the cable connector 190 and the control unit 700 can include a male member e.g., pin(s), prong(s), etc., and the securing member 196, 708 of the other of the cable connector 190 and the control unit 700 can include a correspondingly sized and shaped female member, e.g., hole(s), blind bore(s), etc.

The control unit configured to releasably connect to the cable connector 190 can have a variety of configurations, as discussed above. FIG. 2 illustrates one implementation of such a control unit 160 schematically. The control unit 700 of FIGS. 15 and 16 is one implementation of the control unit 160.

Figure 15:
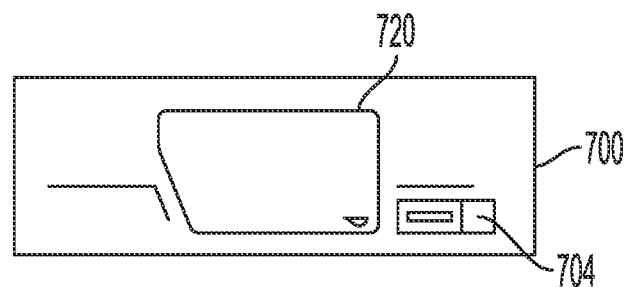
FIG. 15 is a front view of the control unit of FIG. 14.
Figure 16:
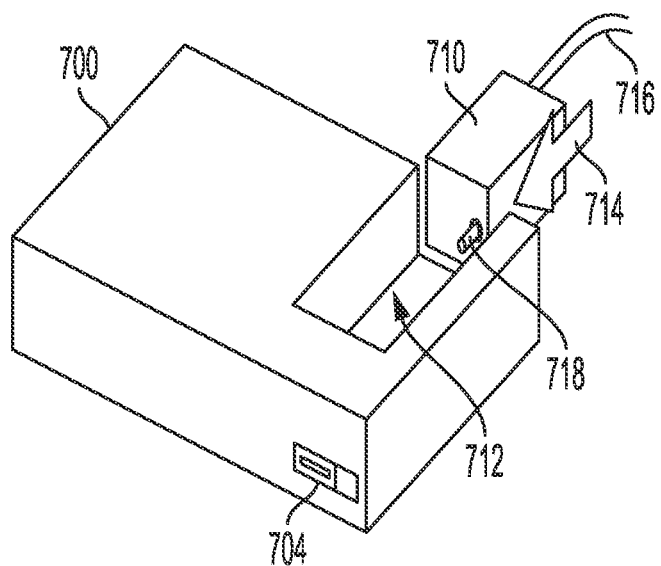
FIG. 16 is a perspective view of the control unit of FIG. 14 and of one embodiment of a cartridge.

In the exemplary implementation of FIGS. 15 and 16, the control unit 700 includes a pump, but in other implementations, the pump can be a separate unit configured to operably couple to the control unit such as shown in FIG. 2 with the pump 134 and the control unit 160. The pump of the control unit 700 includes a peristaltic pump in this illustrated implementation, but the pump can have other configurations. The pump of the control unit 700 is generally configured and used similar to the pump 134 of FIG. 2. The control unit 700 is configured to releasably couple to a cartridge (also referred to herein as a "cassette") configured to operably couple to the pump of the control unit 700. FIG. 16 illustrates one implementation of such a cartridge 710. The control unit 700 includes a cartridge holder 712 configured to releasably seat the cartridge 710 therein. The cartridge 710 and the cartridge holder 712 have complementary rectangular shapes in this illustrated implementation but can have other complementary shapes. FIG. 16 shows the cartridge 710 not yet seated in the cartridge holder 712. An arrow 714 shows a direction of insertion for the cartridge 710 into the cartridge holder 712. The cartridge 710, once seated in the cartridge holder 712, is configured to be removed therefrom in a direction opposite to that of the arrow 714.

Tubing 716 extends from the cartridge 710 and is configured to couple to a fluid source that is generally configured and used similar to the fluid source 136 of FIG. 2. With the cassette 710 operably coupled to the control unit 700, the pump of the control unit 700 is configured to pump fluid from the fluid source, through the tubing 716 to the fluid connector 706, and out of the control unit 700 through the fluid connector 706 into the fluid connector 194 of the cable assembly 106, through which the fluid is pumped into the second cable 193, e.g., the second conduit thereof, for output from the arthroscope 100. The cassette 710 can have a variety of configurations. Exemplary implementations of cassettes are further described in U.S. Pat. No. 7,857,792 entitled "Cassette For Irrigation Or Aspiration Machine For Endoscopy" issued Dec. 28, 2010, which is hereby incorporated by reference in its entirety.

The tubing 716 is in fluid communication with an outlet port 718 of the cartridge 710. The control unit 700 includes an inlet port (obscured in FIG. 16) configured to operably couple to the outlet port 718 in a fluidically sealed relationship. With the cartridge 710 coupled to the control unit 700, the outlet port 718 is configured to be in fluid communication with the control unit's fluid connector 706. Fluid can therefore be pumped from the fluid source, into the cartridge 710 through the tubing 716, out of the cartridge 710 and into the control unit 700 through the outlet port 718, and out of the control unit 700 through the fluid connector 706.

The cartridge 710 is configured to be disposable, e.g., being disposed as medical waste or being fully or partially recycled. The cartridge 710 can thus be disposed after a single use, e.g., after use with a patient in a surgical procedure. The control unit 700 is configured to be reusable and can thus be used in a plurality of surgical procedures each performed on a different patient. The control unit 700 includes elements, such as a processor, a memory, the pump, etc., that are typically more expensive and/or more complicated to manufacture and assemble than elements of the cartridge 710, e.g., an outer housing, the tubing 716, etc. The control unit 700 being reusable may therefore allow the more expensive and/or more complicated elements thereof to be reused instead of having to be disposed of after a single use. The control unit 700 being configured to releasably couple to a cartridge may allow the control unit 700 to couple to a variety of different cartridges, such as cartridges each configured to operably couple to a different type of fluid source, cartridges each including different size tubing, etc., thereby allowing a surgeon and/or other medical personnel to choose a cartridge most appropriate for a particular surgical procedure in which the cartridge will be used.

Figure 17:
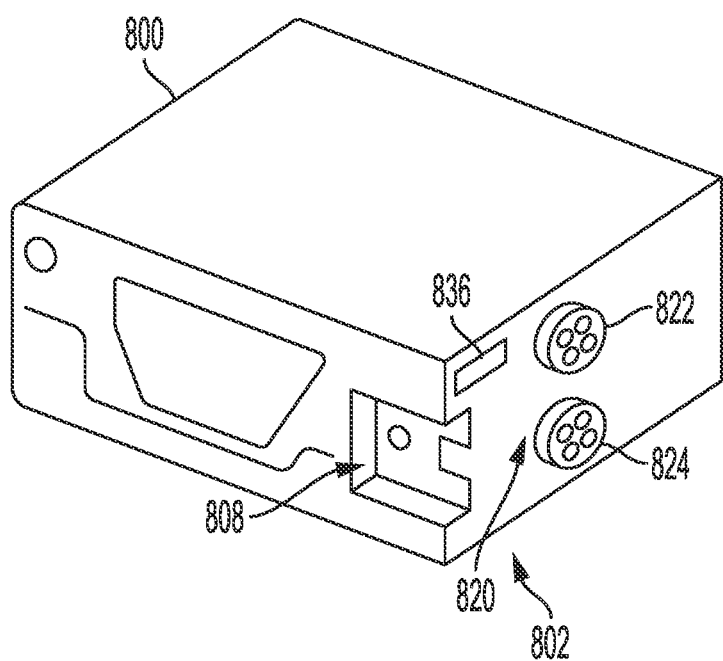
FIG. 17 is a perspective view of another implementation of a control unit.
Figure 18:
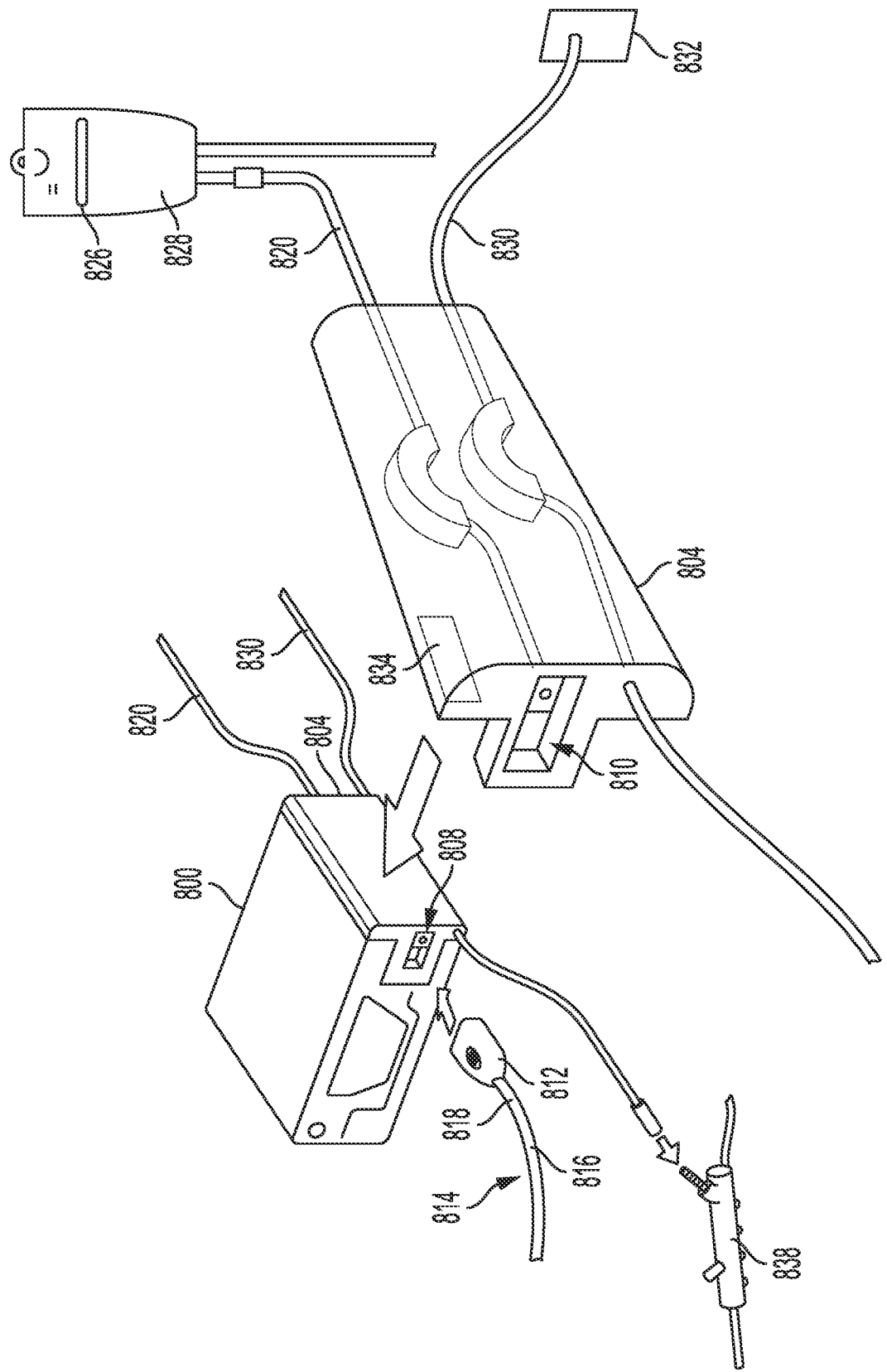
FIG. 18 is a perspective view of the control unit of FIG. 17 operably coupled to another implementation of a cartridge.

FIGS. 17 and 18 illustrate another implementation of a control unit 800 configured to operably couple to a cable connector. The control unit 800 is another implementation of the control unit 160 of FIG. 2 and is generally configured and used similar to the control unit 700 of FIGS. 15 and 16.

The control unit 700 of FIGS. 15 and 16 is configured as a back-loading unit in which a cartridge, e.g., the cartridge 710, is configured to be coupled to the control unit 700 at a back of the control unit 700. A front of the control unit 700 from which a cable assembly, e.g., the cable assembly 106, extends is typically desirable to be accessible and visually observable during use of the control unit 700, e.g., to facilitate connection and disconnection of the cable assembly to and from the control unit 700 and to facilitate user viewing of a user interface 720 on the front of the control unit 700 configured to receive user inputs and/or display information to a user. The control unit 700 being back-loading may facilitate this accessibility and visual observation by having the cartridge 710 and the tubing 716 be on the opposite side of the control unit 700 from the cable port 704 and user interface. The control unit 800 of FIGS. 17 and 18 is configured as a side-loading unit in which a cartridge is configured to be coupled to the control unit 800 at a side of the control unit 800. The side is shown as a right side of the control unit 800 in the illustrated implementation but can instead be on a left side. The control unit 800 being side-loading may still allow for the accessibility and visual observation of the control unit 800 while providing the control unit's cartridge holder 802 at a location that may be easier for a user to access before, during, and/or after a surgical procedure. A control unit can be used while on a cart, shelf, or other support member that has a back surface, abuts a wall at its back, or faces a wall at its back. The back of the control unit may thus in at least some circumstances be more difficult for a user to access than a side of the control unit. The control unit 800 being side-loading may thus ease connection and disconnection of a cartridge to and from the control unit 800 by being at a more easily accessible location to a user than with a back-loading control unit.

The control unit 800 includes a cartridge holder 802 that is generally configured and used similar to the cartridge holder 712 of the control unit 700. One implementation of a cartridge 804 configured to operably couple to the control unit 800 by coupling to the cartridge holder 802 is illustrated in FIG. 18. The cartridge 804 is generally configured and used similar to the cartridge 710 of FIG. 16. As mentioned above, exemplary implementations of cartridges are further described in U.S. Pat. No. 7,857,792 entitled "Cassette For Irrigation Or Aspiration Machine For Endoscopy" issued Dec. 28, 2010.

In the illustrated implementation of FIGS. 17 and 18, a cable port 806 configured to operably couple to a cable connector is defined by a first cable port 808 of the control unit 800 and a second cable port 810 of the cartridge 804. With the cartridge 804 operably coupled to the control unit 806, e.g., with the cartridge 804 received by the cartridge holder 802, the first and second cable ports 808, 810 are aligned with one another to form the cable port 806 configured to releasably couple to a cable connector.

FIG. 18 illustrates one implementation a cable connector 812 configured to operably couple to the cable port 806. The cable connector 812 is at the proximal end of a cable assembly 814 and is configured to operably couple to the control unit 800 or other implementation of a control unit described herein. The cable assembly 814 is generally configured and used similar to the cable assembly 106 of FIGS. 1 and 2. The cable assembly 814 in this illustrated implementation includes a first cable 816 and a second cable 818. The first cable 816 includes a first conduit including electrical wire(s) and is configured and used similar to that discussed above regarding the first cable 130 of the cable assembly 106. The second cable 818 includes a second conduit configured to provide irrigation fluid from a fluid source and is configured and used similar to that discussed above regarding the second conduit of the second cable 132 of the cable assembly 106. In this illustrated implementation, the second cable 818 does not include a third conduit for suctioning.

The cable connector 812 includes an electrical connector (obscured in FIG. 18) that is configured and used similar to the electrical connector 192 of FIG. 13, includes a fluid connector (obscured in FIG. 18) that is configured and used similar to the fluid connector 194 of FIG. 13, and includes a securing member (obscured in FIG. 18) that is configured and used similar to the securing member 196 of FIG. 13. With the electrical connector of the cable connector 812 operably coupled to the control unit's electrical connector (obscured in FIG. 18), the control unit 800 can provide power to the arthroscope via the first cable 816, and data can be communicated via the first cable 816 from the arthroscope to the control unit 800 and/or from the control unit 800 to the arthroscope. With the fluid connector of the cable connector 812 operably coupled to the control unit's fluid connector (obscured in FIG. 18), the control unit 800 can provide fluid irrigation via the second cable 818. As in the implementation of FIG. 14, the cable port 806 can include a corresponding securing member (obscured in FIG. 18) that is configured to securely, releasably engage the securing member of the cable connector 812.

In the implementation of FIGS. 17 and 18, the control unit 800 includes a pump 820, but in other implementations, the pump can be a separate unit configured to operably couple to the control unit such as shown in FIG. 2 with the pump 134 and the control unit 160. The pump 820 includes a first peristaltic pump 822 and a second peristaltic pump 824 in this illustrated implementation, but the pump can have other configurations. The pump 820 is generally configured and used similar to the pump 134 of FIG. 2.

Irrigation tubing 820 extends from the cartridge 804 and is generally configured and used similar to the tubing 716 of FIG. 15. The irrigation tubing 820 is configured to couple to a fluid source 826 that is generally configured and used similar to the fluid source 136 of FIG. 2. The fluid source 826 includes an intravenous (IV) bag in this illustrated implementation but can have other configurations. With the cassette 804 operably coupled to the control unit 800, the first pump 822 is configured to pump fluid 828 from the fluid source 826, through the irrigation tubing 820 to the fluid connector of the cartridge 804 at the cable port 806, and out of the cartridge 804 through the fluid connector into the fluid connector of the cable assembly 814, through which the fluid 828 is pumped into the second cable 818, e.g., the second conduit thereof, for output from the arthroscope. The fluid 828 includes saline in this illustrated implementation but can include water or other irrigation fluid.

The cartridge 804 in this illustrated implementation includes suction tubing 830 extending therefrom. The suction tubing 830 is configured to operably couple to an outflow outlet 832 through which solid and/or liquid matter suctioned through the suction tubing 830 can be collected. The outflow outlet 832 in this illustrated implementation is a wall outlet operably coupled to a collection container or other containment mechanism but can have other configurations. With the cassette 804 operably coupled to the control unit 800, the second pump 824 is configured to provide suction force to the suction tubing 830 so as to provide suction in a proximal direction toward the outflow outlet 832. The suction tubing 830 is configured to be operably coupled to a surgical tool 838 configured to provide suction at the surgical site via the suction force provided through the suction tubing 830. The surgical tool 838 is a shaver in this illustrated embodiment, but various surgical tools with suction functionality can be used, as will be appreciated by a person skilled in the art. The surgical tool 838 can be fixedly coupled to the suction tubing 830, and thus to the cartridge 804, or the suction tubing 830 can be configured to releasably coupled to the surgical tool 838.

The suction tubing 830 being releasably couplable to the surgical tool 838, as in this illustrated embodiment, may allow for the suction tubing 830 and the cartridge 804 to be disposable while allowing the surgical tool to be reusable.

The cartridge 804 and the control unit 800 in this illustrated implementation include corresponding circuit connections 834, 836. The circuit connection 834 of the cartridge 804 is configured to operably couple to the circuit connection 836 of the control unit 800 with the cartridge 804 received by the cartridge holder 802. The circuit connections 834, 836 being operably coupled together allows for various functionality, such as the control unit 800 being able to detect coupling of the cartridge 804 to the cartridge holder 802; the control unit 800 being able to receive identification information from the cartridge holder 802 that the control unit 800 can be configured to use to, e.g., verify authenticity of the cartridge 804, verify compatibility of the cartridge 804 with the control unit 800, trigger the control unit 800 being able to receive pumping information from the cartridge holder 802 that the control unit 800 can be configured to use to control the first and second pumps 822, 824 to safely control flow through the irrigation and suction tubing 820, 830, trigger the control unit 800 to turn on any light(s) of the arthroscope operably coupled thereto, etc.

The cartridge 804 is configured to be disposable similar to that discussed above regarding the cartridge 710 of FIG. 16. The control unit 800 is configured to be reusable similar to that discussed above regarding the control unit 700 of FIGS. 15 and 16.

Figure 19:
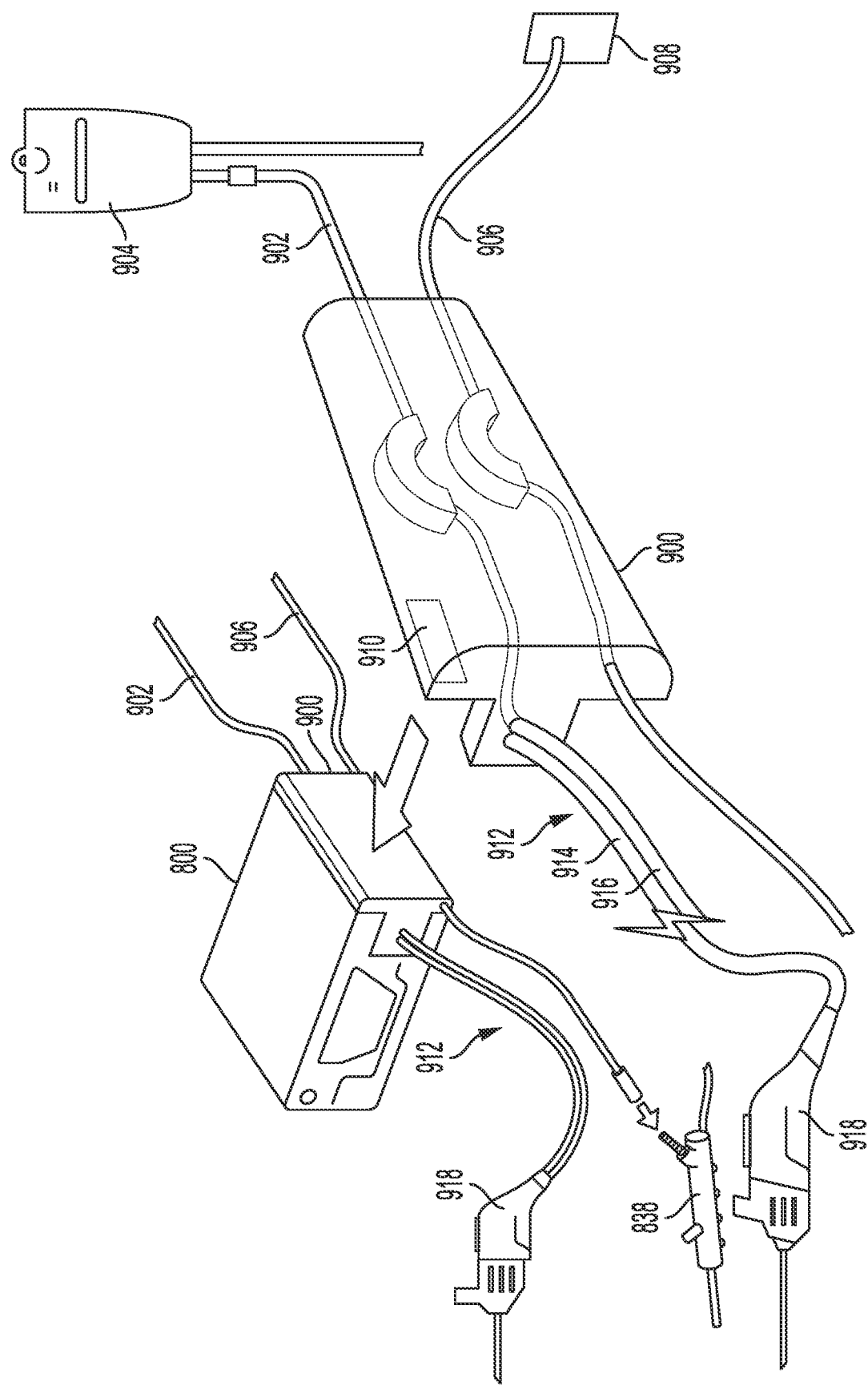
FIG. 19 is a perspective view of the control unit of FIG. 17 operably coupled to another implementation of a cartridge.

FIG. 19 illustrates another implementation of a cartridge 900 configured to operably couple to the control unit 800 of FIG. 17. The cartridge 900 is generally configured and used similar to the cartridge 804 of FIG. 18, e.g., includes irrigation tubing 902 configured to couple to a fluid source 904 and configured to be pumped by the first pump 822, includes suction tubing 906 configured to couple to an outflow outlet 908 and configured to be pumped by the second pump 824, and includes a circuit connection 910 configured to couple to the control unit's circuit connection 836. The suction tubing 906 is configured to be operably coupled to the surgical tool 838, similar to that discussed above regarding the suction tubing 830 of FIG. 18. The cartridge 900 is configured to be disposable similar to that discussed above regarding the cartridge 710 of FIG. 16. As mentioned above, exemplary implementations of cartridges are further described in U.S. Pat. No. 7,857,792 entitled "Cassette For Irrigation Or Aspiration Machine For Endoscopy" issued Dec. 28, 2010.

In the illustrated implementation of FIG. 19, a cable assembly of an arthroscope is not operably coupled to a cable port defined by the control unit 800 and the cartridge 904 when coupled to the control unit 800. Instead, a cable assembly 912 including first and second cables 914, 916 extends from the cartridge 904. The cable assembly 912 is configured to operably couple to an arthroscope 918. The arthroscope 918 is configured and used similar to the arthroscope 100 of FIGS. 1 and 2. The arthroscope 918 is configured to releasably couple to the cable assembly 912 in this illustrated implementation but can, in other implementations, be fixedly coupled to the cable assembly 912. The first and second cables 914, 916 are configured and used similar to the first and second cables 130, 132 of FIGS. 1 and 2. The first cable 914 includes a first conduit including electrical wire(s) and is configured and used similar to that discussed above regarding the first cable 130 of the cable assembly 106. The second cable 916 includes a second conduit configured to provide irrigation fluid from a fluid source and is configured and used similar to that discussed above regarding the second conduit of the second cable 132 of the cable assembly 106. In this illustrated implementation, the second cable 916 does not include a third conduit for suctioning. Instead, as mentioned above, the suction tubing 930 is configured to provide suction functionality at a surgical site via the surgical tool 838.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the arthroscopic medical implements and assemblies and methods based on the above-described embodiments. Accordingly, this disclosure is not to be limited by what has been particularly shown and described, except as indicated by the appended claims. All publications and references cited herein are expressly incorporated herein by reference in their entirety.

The present disclosure has been described above by way of example only within the context of the overall disclosure provided herein. It will be appreciated that modifications within the spirit and scope of the claims may be made without departing from the overall scope of the present disclosure.

What is claimed is:

1. A surgical system, comprising:
   an arthroscope including
      a handle;
      a cable assembly extending proximally from the handle, the cable assembly including a first cable, a second cable, and a cable connector at a proximal end of the cable assembly, and
      an elongate shaft extending distally from the handle, a first lumen and a second lumen extending through the shaft, the first lumen being in communication with a first conduit of the first cable, and the second lumen being in communication with a second conduit of the second cable;
   a control unit configured to releasably couple to the cable connector, the control unit including a pump, and, with the control unit releasably coupled to the cable connector, the control unit is configured to provide electrical power to the arthroscope via the first cable and the first conduit; and a cartridge configured to releasably couple to the control unit, the cartridge including tubing;

wherein, with the cartridge releasably coupled to the control unit, the pump is configured to cause fluid flow in the tubing, the second conduit, and the second cable;

the tubing is configured to operably couple to a fluid source containing an irrigation liquid therein; and the fluid flow includes flow of the irrigation liquid from the fluid source through the tubing to the cartridge.

2. The system of claim 1, wherein, with the cartridge releasably coupled to the control unit and second tubing of the cartridge operably coupled to a surgical tool configured to deliver a suction force to a surgical site, the pump is configured to cause a suction force to be provided in the second tubing such that the surgical tool delivers the suction force.

3. The system of claim 1, wherein the cable assembly includes a third cable;

a third lumen extends through the shaft, the third lumen being in communication with a third conduit of the third cable;

the control unit includes a second pump;

the cartridge includes second tubing; and with the cartridge releasably coupled to the control unit, the second pump is configured to cause the suction force to be provided in the second tubing, the third conduit, and the third cable.

4. The system of claim 1, wherein the arthroscope includes an optical sensor at a distal portion of the shaft, the optical sensor being configured to gather image data; and the electrical power provided to the arthroscope is configured to power the optical sensor.

5. The system of claim 4, wherein the arthroscope includes an inertial sensor configured to gather orientation data that indicates an orientation of the image data gathered by the optical sensor; and the control unit is configured to receive the gathered image data via a wire extending through the first conduit and the first cable.

6. The system of claim 5, wherein the control unit is configured to modify an image of the received image data using the received orientation data, and is configured to cause the modified image to be output to a display unit.

7. The system of claim 6, wherein the modifying includes rotating the image to a predetermined desired orientation based on the orientation data.

8. The system of claim 6, wherein the control unit is configured to modify the image using the orientation data in real time with rotation of the handle about a common longitudinal axis of the handle and the shaft; and the control unit is configured to cause the modified image to be output to the display unit in real time with the rotation of the handle.

9. The system of claim 1, wherein with the cartridge releasably coupled to the control unit, the tubing of the cartridge is configured to operably couple with the pump of the control unit.

10. A surgical method, comprising:

providing electrical power from the control unit of the surgical system of claim 1, which is releasably coupled to the arthroscope of the surgical system of claim 1 and is releasably coupled to the cartridge of the surgical system of claim 1, to provide electrical power to the arthroscope via the first cable, wherein the cartridge is releasably seated in a cartridge holder of the control unit; and causing, using the pump of the control unit, fluid flow in the tubing of the cartridge and thereby cause fluid flow in the second cable.

11. The method of claim 10, wherein the fluid flow includes the flow of the irrigation liquid.

12. The method of claim 11, further comprising, causing, using a second pump of the control unit, a suction force to be provided in second tubing of the cartridge such that a surgical tool operably coupled to the second tubing delivers the suction force to a surgical site.

13. The method of claim 10, further comprising causing, using a second pump of the control unit, flow of an irrigation liquid in second tubing of the cartridge and thereby cause a suction force in a third cable of the cable assembly.

14. The method of claim 10, further comprising gathering image data using an optical sensor at a distal portion of the arthroscope, the control unit receiving the gathered image data via a wire extending through the first cable; and gathering orientation data using an inertial sensor.

15. The method of claim 14, further comprising the control unit modifying, in real time with performance of a surgical procedure, an image of the received image data using the received orientation data; and causing, using the control unit, the modified image to be displayed on a display unit in real time with the performance of the surgical procedure.

16. The method of claim 15, wherein the modifying includes rotating the image to a predetermined desired orientation based on the orientation data.

17. The method of claim 15, wherein the modifying and the causing of the modified image to be displayed occurs in real time with rotation of the handle of the arthroscope about a common longitudinal axis of the handle and the elongate shaft of the arthroscope.

18. A surgical system, comprising:

an arthroscope including a handle;

a cable assembly extending proximally from the handle, the cable assembly including a first cable, a second cable, and a cable connector at a proximal end of the cable assembly, and an elongate shaft extending distally from the handle, a first lumen and a second lumen extending through the shaft, the first lumen being in communication with a first conduit of the first cable, and the second lumen being in communication y a second conduit of the second cable;

a control unit configured to releasably couple to the cable connector, the control unit including a pump, and, with the control unit releasably coupled to the cable connector, the control unit is configured to provide electrical power to the anthroscope via the first cable and the first conduit; and a cartridge configured to releasably couple to the control unit, the cartridge including tubing;

wherein, with the cartridge releasably coupled to the control unit, the pump is configured to cause fluid flow in the tubing, the second conduit, and the second cable;

the cartridge includes an outer housing having a shape;

the control unit includes a cartridge holder defining a cut-out in the control unit, the cut-out being configured to releasably seat the cartridge therein; and the cut-out has a shape that is complementary to the shape of the outer housing of the cartridge.

19. The system of claim 18, wherein causing the fluid flow includes causing a suction force to be provided in the tubing, the second conduit, and the second cable.

20. The system of claim 18, wherein the tubing is configured to operably couple to a fluid source containing an irrigation liquid therein; and the fluid flow includes flow of the irrigation liquid from the fluid source through the tubing to the cartridge.

\* \* \* \* \*